United States Patent
Hashimoto et al.

(10) Patent No.: US 9,067,862 B2
(45) Date of Patent: Jun. 30, 2015

(54) CONDENSED POLYCYCLIC COMPOUND AND ORGANIC LIGHT EMITTING DEVICE USING THE SAME

(75) Inventors: Masashi Hashimoto, Tokyo (JP); Satoshi Igawa, Fujisawa (JP); Naoki Yamada, Inagi (JP); Takayuki Horiuchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 39 days.

(21) Appl. No.: 12/262,084

(22) Filed: Oct. 30, 2008

(65) Prior Publication Data

US 2009/0121623 A1 May 14, 2009

(30) Foreign Application Priority Data

Nov. 2, 2007 (JP) ................................ 2007-286105

(51) Int. Cl.
*H01L 51/52* (2006.01)
*C07C 15/20* (2006.01)
(Continued)

(52) U.S. Cl.
CPC .................. *C07C 25/22* (2013.01); *C07C 15/20* (2013.01); *C07C 211/61* (2013.01);
(Continued)

(58) Field of Classification Search
USPC ......................................................... 428/690
See application file for complete search history.

(56) References Cited

U.S. PATENT DOCUMENTS 7,175,922 B2  2/2007  Jarikov
7,183,010 B2  2/2007  Jarikov (Continued)

FOREIGN PATENT DOCUMENTS

JP   2001-102172 A   4/2001
JP   2003338377 A * 11/2003 ............. H05B 33/22

(Continued)

OTHER PUBLICATIONS

Machine English translation of JP 2001-102172 A. Aug. 6, 2013.*

(Continued)

*Primary Examiner* — J. L. Yang
(74) *Attorney, Agent, or Firm* — Canon U.S.A.Inc., IP Division

(57) ABSTRACT

A condensed polycyclic compound is represented by the following Formula [1]:

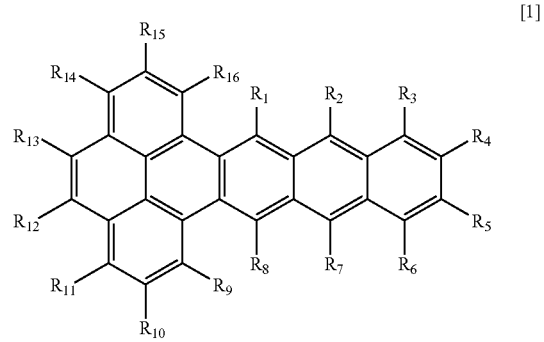

[1]

wherein in Formula [1], $R_1$ to $R_{16}$ each represent a hydrogen atom, a halogen atom, an alkyl group having 1 to 20 carbon atoms, a substituted amino group, an aryl group that may optionally have a substituent group, or a heterocyclic group that may optionally have a substituent group, provided that at least one of $R_1$, $R_2$, $R_7$ and $R_8$ is an aryl group that may optionally have a substituent group, or a heterocyclic group that may optionally have a substituent group.

6 Claims, 3 Drawing Sheets

(51) Int. Cl.

| | | |
|---|---|---|
| *C07C 25/22* | (2006.01) | |
| *C07C 211/61* | (2006.01) | |
| *C07D 471/04* | (2006.01) | |
| *C07D 209/10* | (2006.01) | |
| *C07D 213/24* | (2006.01) | |
| *C07D 217/02* | (2006.01) | |
| *C07D 217/12* | (2006.01) | |
| *C07D 221/08* | (2006.01) | |
| *C07D 239/26* | (2006.01) | |
| *C07D 263/32* | (2006.01) | |
| *C07D 277/66* | (2006.01) | |
| *C07D 307/91* | (2006.01) | |
| *C07D 333/08* | (2006.01) | |
| *C07D 519/00* | (2006.01) | |
| *H01L 51/00* | (2006.01) | |
| *H01L 51/50* | (2006.01) | |

(52) U.S. Cl.
CPC ......... *C07C 2103/54* (2013.01); *C07D 209/10* (2013.01); *C07D 213/24* (2013.01); *C07D 217/02* (2013.01); *C07D 217/12* (2013.01); *C07D 221/08* (2013.01); *C07D 239/26* (2013.01); *C07D 263/32* (2013.01); *C07D 277/66* (2013.01); *C07D 307/91* (2013.01); *C07D 333/08* (2013.01); *C07D 471/04* (2013.01); *C07D 519/00* (2013.01); *H01L 51/0056* (2013.01); *H01L 51/0058* (2013.01); *H01L 51/5012* (2013.01); *H01L 51/5048* (2013.01)

(56) References Cited

U.S. PATENT DOCUMENTS

| | | | | |
|---|---|---|---|---|
| 2004/0076853 | A1* | 4/2004 | Jarikov | 428/690 |
| 2004/0164668 | A1* | 8/2004 | Kanno et al. | 313/500 |
| 2004/0253389 | A1* | 12/2004 | Suzuki et al. | 428/1.1 |
| 2006/0214553 | A1* | 9/2006 | Nagara et al. | 313/483 |
| 2007/0104977 | A1* | 5/2007 | Arakane et al. | 428/690 |
| 2010/0025661 | A1* | 2/2010 | Wang et al. | 257/40 |

FOREIGN PATENT DOCUMENTS

| | | |
|---|---|---|
| JP | 2003-347058 A | 12/2003 |
| WO | 2004/043901 A | 5/2004 |
| WO | 2005/040303 A | 5/2005 |

OTHER PUBLICATIONS

Jie-Hiu, Dong Zhang, and Frank W. Harris, "Ruthenium(III) Chloride Catalyzed Oxidation of Pyrene and 2,7-Disubstitued Pyrenes: An Efficient, One-Step Synthesis of Pyrene-4,5-diones and Pyrene-4,5,9,10-tetraones", J. Org. Chem., vol. 70, No. 2, 2005, pp. 707-708.

Robert A. Pascal, Jr., et al., "Synthesis and Structure of Longitudinally Twisted Polycyclic Aromatic Hydrocarbons", J. Am. Chem. Soc, vol. 109, No. 15, 1987, pp. 4660-4665.

* cited by examiner

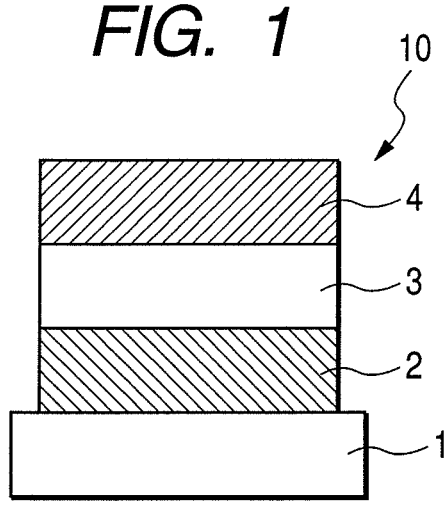
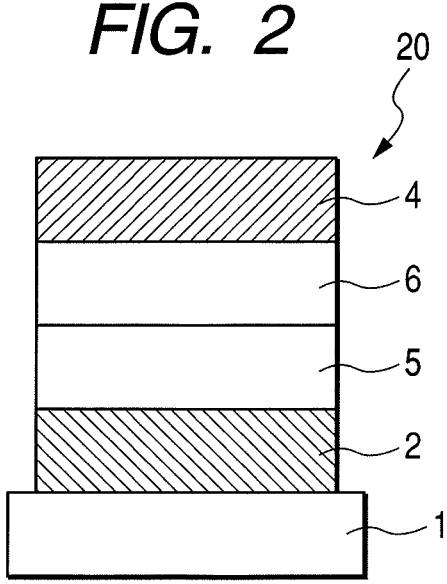

CONDENSED POLYCYCLIC COMPOUND AND ORGANIC LIGHT EMITTING DEVICE USING THE SAME

BACKGROUND OF THE INVENTION

1. Field of the Invention

The present invention generally relates to a condensed polycyclic compound and a light emitting device using the same.

2. Description of the Related Art

Recent progress in the development of organic light emitting devices has been remarkable, and includes the development of relatively high brightness at a fairly low applied voltage, diversification of the wavelength of the emitted light, high-speed response, and a reduction in the thickness and weight of the light emitting device. From this, the organic light emitting device appears to show promise for broader use.

However, there remains a need for the development of optical power with increased brightness or higher conversion efficiency. In addition, there remains a need for improvement in aspects such as durability, to reduce deterioration that can occur with use over long periods of time, and to reduce deterioration by atmospheric gas containing oxygen and/or moisture. Furthermore, in the case of application to full color displays, there remains a need for emission of blue, green and red lights with increased color purity.

Some studies have been conducted on aromatic compounds and condensed polycyclic aromatic compounds as fluorescent organic compounds usable as materials that constitute the light emitting layer, electron transport layer and the like. However, compounds having fully satisfactory light emission brightness and durability have not yet been obtained.

Japanese Patent Application Laid-Open No. 2003-347058, WO2005/040303, and WO2004/043901 disclose examples of aromatic compounds and condensed polycyclic aromatic compounds as materials that constitute organic light emitting devices. Also, Japanese Patent Application Laid-Open No. 2003-347058, WO2005/040303, and WO2004/043901 disclose the application of certain condensed polycyclic aromatic compounds to organic light emitting devices.

Accordingly, in order to achieve satisfactory performance of organic light emitting devices in display apparatuses, such as display screens, an enhancement in the durability of the devices may need to be obtained.

SUMMARY OF THE INVENTION

In one aspect, a condensed polycyclic compound according to the present invention is represented by the following Formula [1];

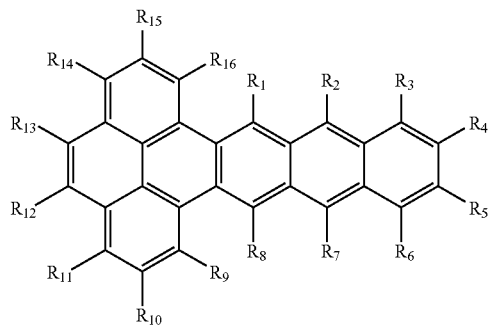

[1]

wherein in Formula [1], $R_1$ to $R_{16}$ each represent a hydrogen atom, a halogen atom, an alkyl group having 1 to 20 carbon atoms, a substituted amino group, an aryl group that may optionally have a substituent group, or a heterocyclic group that may optionally have a substituent group, provided that at least one of $R_1$, $R_2$, $R_7$ and $R_8$ is an aryl group that may optionally have a substituent group, or a heterocyclic group that may optionally have a substituent group.

Further features of the present invention will become apparent from the following description of exemplary embodiments with reference to the attached drawings.

BRIEF DESCRIPTION OF THE DRAWINGS

FIG. 1 is a cross-sectional view illustrating a first embodiment of the organic light emitting device according to the present invention.

FIG. 2 is a cross-sectional view illustrating a second embodiment of the organic light emitting device according to the present invention.

DESCRIPTION OF THE EMBODIMENTS

Figure 3:
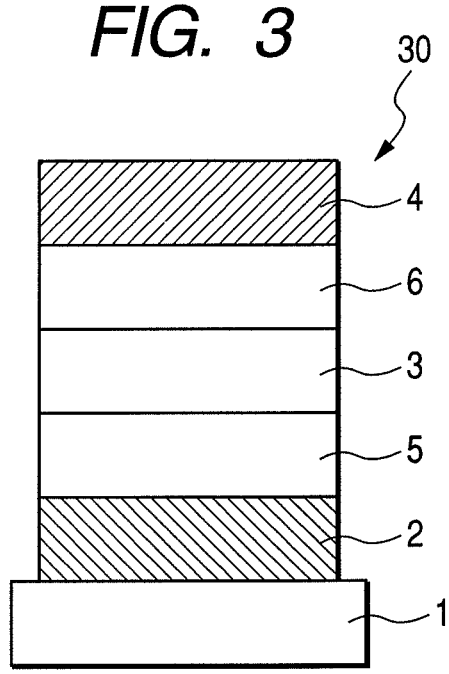
FIG. 3 is a cross-sectional view illustrating a third embodiment of the organic light emitting device according to the present invention.

Hereinbelow, the present invention is described in detail. First, a condensed polycyclic compound according to one embodiment of the present invention is described.

In one embodiment, the condensed polycyclic compound according to the present invention is represented by the following Formula [1].

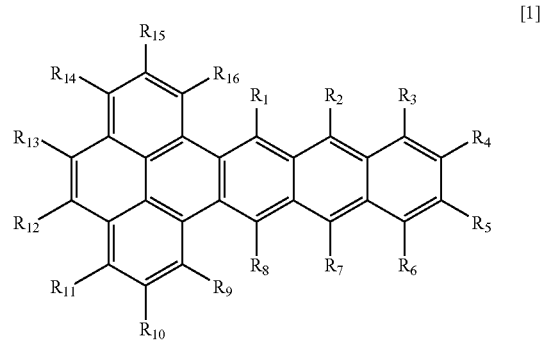

[1]

In Formula [1], $R_1$ to $R_{16}$ each represent a hydrogen atom, a halogen atom, an alkyl group having 1 to 20 carbon atoms, a substituted amino group, an aryl group that may optionally have a substituent group, or a heterocyclic group that may optionally have a substituent group, provided that at least one of $R_1$, $R_2$, $R_7$ and $R_8$ is an aryl group that may optionally have a substituent group, or a heterocyclic group that may optionally have a substituent group. In one version, at least one of $R_1$ and $R_8$ is an aryl group that may optionally have a substituent group, or a heterocyclic group that may optionally have a substituent group.

In one embodiment, the halogen atom represented by $R_1$ to $R_{16}$ may be, for example, a fluorine atom, a chlorine atom or a bromine atom. As an example, when an organic light emitting device is prepared by a vacuum vapor deposition method, a suitable halogen atom may be a fluorine atom.

Examples of the alkyl group represented by $R_1$ to $R_{16}$ can include, but are not limited to, a methyl group, an ethyl group, an n-propyl group, an iso-propyl group, an n-butyl group, a tert-butyl group, an octyl group and a cyclohexyl group.

In one version, when the alkyl group has two or more carbon atoms, one or two or more methylene (—$CH_2$—) groups in the alkyl group that are not adjacent to each other may be substituted with —O— to form, for example, a methoxy group or an ethoxy group.

Also, in another version, some or all of the hydrogen atoms in the alkyl group may be substituted with a fluorine atom to form, for example, a trifluoromethyl group or a trifluoromethoxy group.

In one embodiment, the alkyl group may be, for example, a methyl group, a tert-butyl group, a cyclohexyl group or a trifluoromethyl group, and may be selected to provide a suitable electric conductivity and glass transition temperature. For example, the alkyl group may be a methyl group, a tert-butyl group or a trifluoromethyl group. As another example, the alkyl group may be a methyl group or a tert-butyl group.

In one embodiment, the substituted amino group represented by $R_1$ to $R_{16}$ may be a dimethylamino group, a diphenylamino group or a ditolylamino group, and may be selected to provide a suitable electric conductivity and glass transition temperature. For example, the substituted amino group represented by $R_1$ to $R_{16}$ may be a diphenylamino group.

Examples of the aryl group represented by $R_1$ to $R_{16}$ may include, but are not limited to, a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

In one embodiment, the aryl group may be, for example, a phenyl group, a fluorenyl group or a naphthyl group, and may be selected to provide a suitable sublimability. For example, the aryl group may be a phenyl group.

Examples of the heterocyclic group represented by $R_1$ to $R_{16}$ may include, but are not limited to, a thienyl group, a pyrrolyl group, a pyridyl group, a pyrazyl group, a pyrimidyl group, a pyridazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuranyl group, a dibenzothiophenyl group, a carbazolyl group, a benzofuranyl group, a benzothiophenyl group, an indolyl group, a cycloazyl group, a benzoimidazolyl group, a benzothiazolyl group, a benzothiadiazolyl group, a benzoquinolyl group, and an azaindolizyl group.

In one embodiment, the heterocyclic group may be, for example, a pyridyl group, and may be selected to provide suitable sublimability.

The substituent group that either or both of the aryl group and the heterocyclic group mentioned above may optionally be substituted by is not particularly limited and specific examples thereof may include, but are not limited to, a halogen atom, an alkyl group having 1 to 20 carbon atoms, a substituted amino group, an aryl group and a heterocyclic group. In one embodiment, the substituent group may be a halogen atom, an alkyl group having 1 to 20 carbon atoms or a substituted amino group. Furthermore, in an embodiment where the substituent group is an alkyl group having two or more carbon atoms, one or two or more methylene (—$CH_2$—) groups in the alkyl group that are not adjacent to each other may be substituted with —O—. Also, in another embodiment, some or all of the hydrogen atoms in the alkyl group may be substituted with a fluorine atom. Specific examples of the halogen atom, alkyl group, substituted amino group, aryl group and heterocyclic group may be the same as the specific examples of the halogen atom, alkyl group, substituted amino group, aryl group and heterocyclic group represented by $R_1$ to $R_{16}$ that have been described above.

In one embodiment, the substituent group may be, for example, a fluorine atom, a trifluoromethyl group, a methyl group, an ethyl group, a tert-butyl group, a methoxy group, a dimethylamino group or a tert-butylamino group, and may be selected to provide a suitable glass transition temperature and sublimability. For example, the substituent group may be fluorine, a trifluoromethyl group, a methyl group or a tert-butyl group. As another example, the substituent group may be a methyl group or a tert-butyl group.

In one version, a condensed polycyclic compound according to the present invention can be synthesized by, for example, the routes as shown below. However, the present invention is not limited thereto, and other synthetic routes may also be used.

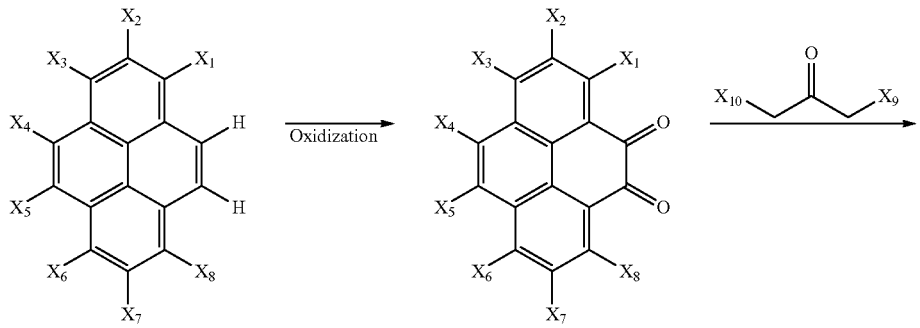

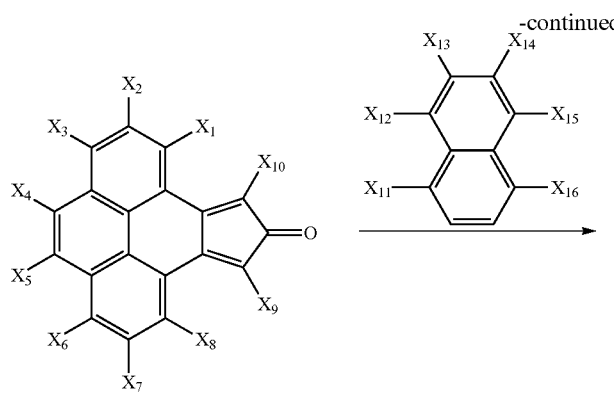
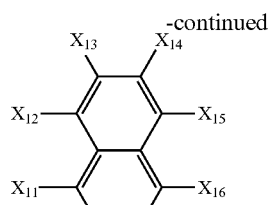
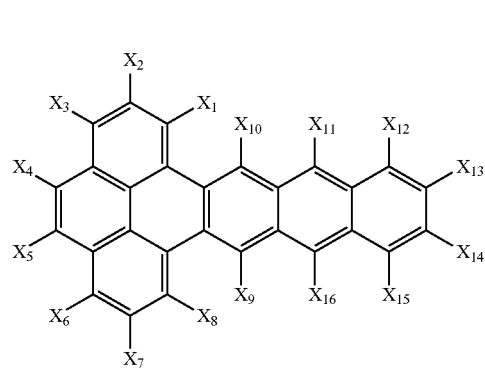

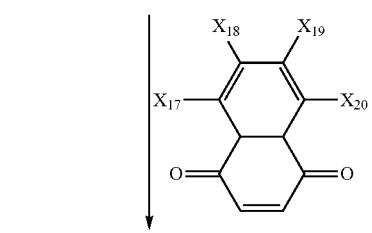

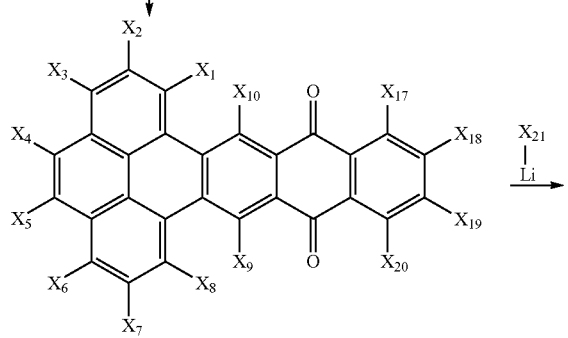
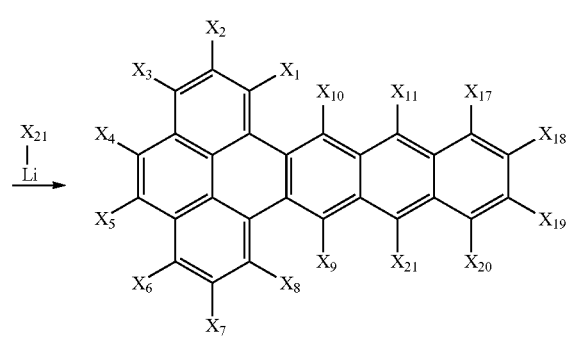

According to one embodiment of the invention, the condensed polycyclic compound can be sufficiently purified so that impurities may be removed. It is believed that reducing contamination by impurities may possibly decrease the deterioration in the light emission that can otherwise occur with the application of electricity. When a polymer compound is used as a constituting material of the organic light emitting device, it can be difficult to remove impurities in the polymer compound. Accordingly, in certain cases, an organic light emitting device containing a polymer compound may be more readily contaminated with impurities, and the life of the device may thus be shortened. However, since the condensed polycyclic compound of the present invention may correspond to a compound having a single molecular weight, impurities may be relatively easily removed by using appropriate purification methods such as, for example, recrystallization, column chromatography, and sublimation purification methods. Accordingly, durability of the organic light emitting device may be improved by using a condensed polycyclic compound in accordance with the present invention as a constituting material for the organic light emitting device.

In one embodiment, the condensed polycyclic compound according to the present invention is a compound comprising a combination of a basic skeleton corresponding to the condensed polycyclic ring represented by Formula [1], and substituent groups represented by $R_1$ to $R_{16}$ in Formula [1].

In one version, the condensed polycyclic compound according to the present invention is a compound that consists of only carbon atoms and hydrogen atoms. When the compound consists of only carbon atoms and hydrogen atoms, it may become less likely that ionic impurities, which are believed to be one of the causes of deterioration in organic light emitting devices with the application of electricity, will become incorporated therein, as compared with a compound containing a heteroatom having a lone electron-pair. The life of an organic light emitting device may this be improved by reducing the contamination of the device by such ionic impurities.

In addition, in one embodiment of the condensed polycyclic compound according to the present invention, at least one of $R_1$, $R_2$, $R_7$ and $R_8$ is an aryl group that may optionally have a substituent group, or a heterocyclic group that may optionally have a substituent group.

In one aspect, the aryl group and the heterocyclic group introduced into these substitution sites are believed to receive strong steric repulsion from the adjacent substituent groups on both sides. Consequently, the planar ring structure corresponding to the aryl group or the heterocyclic group that is introduced as the substituent group may assume a position almost orthogonal to the condensed polycyclic ring, which is a basic skeleton and has a planar ring structure, and may thereby suppress or inhibit stacking properties of the molecule.

As discussed above, the planar ring structure that forms the basic skeleton of the compound (i.e., the condensed polycyclic ring), and the planar ring structure that may be incorporated as a substituent group (aryl group or heterocyclic group) into the compound, may be orthogonal to each other, and thus the stacking properties of the molecule may be reduced. Accordingly, it is believed that the following two effects may occur as described below.

(i) The stability of the organic thin film may be improved by a decrease in crystallinity thereof, and a deterioration of light emission of the device with the application of electricity may thereby be suppressed. This is because crystallization of the organic compound is believed to be a cause of the deterioration of light emission of the device with the application of electricity in an electroluminescence device.

(ii) The concentration quenching, which is a phenomenon in which light emission efficiency decreases due to increased concentration of the guest in the light emitting device, may be suppressed. This is because extinction due to the stacking of the same kind of molecules and formation of excimers is believed to be suppressed by inhibiting or suppressing the stacking properties of the molecule. In addition, a decrease in the light emitting efficiency and change in emitted light color are also believed to be suppressed by inhibiting or suppressing the intermolecular stacking and formation of excimers.

In one embodiment, when a substituent group that is an aryl group or a heterocyclic group is introduced into at least one of $R_1$, $R_2$, $R_7$ and $R_8$, the group may be introduced into at least one of $R_1$ and $R_8$. When these groups are introduced into at least one of $R_1$ and $R_8$, they are believed to receive relatively stronger steric repulsion against the adjacent substituent groups on both sides as compared with the case in which these groups are introduced into at least one of $R_2$ and $R_7$. In one version, aryl groups are introduced into both $R_1$ and $R_8$. In another version, all of $R_1$, $R_2$, $R_7$ and $R_8$ are aryl groups that are selected to provide suitable film characteristics and concentration quenching.

Specific examples of the condensed polycyclic compounds of the present invention are shown below. These are, however, intended only to illustrate suitable examples thereof, and the condensed polycyclic compounds according to the present invention are not intended to be limited thereto.

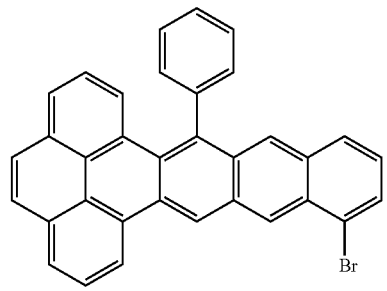

a-1

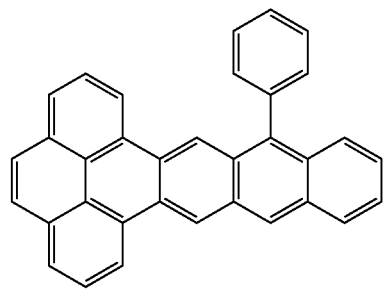

a-2

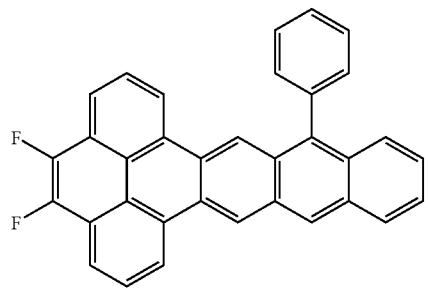

a-3

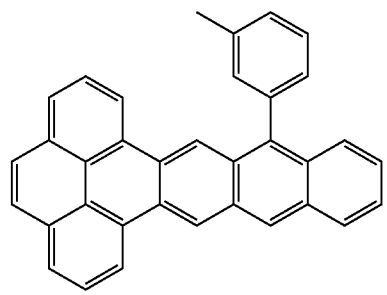

a-4

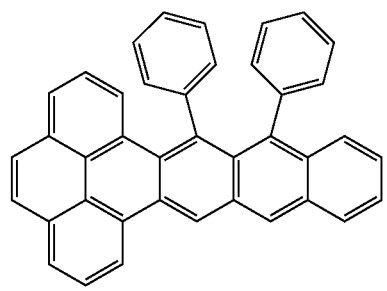

a-5

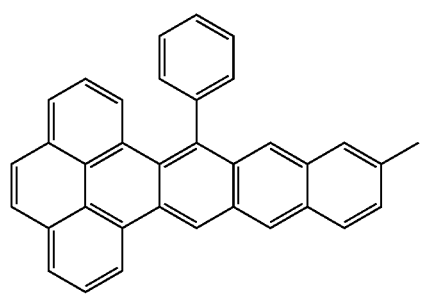

a-6

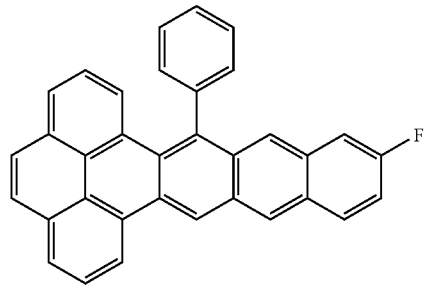

a-7 a-8
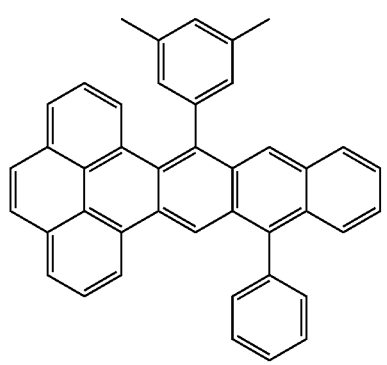
a-9
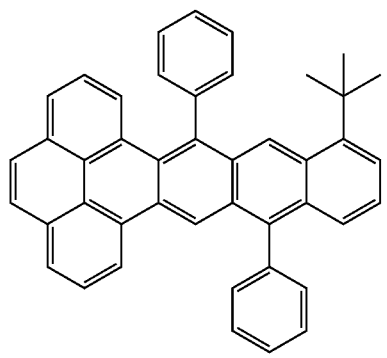
a-10
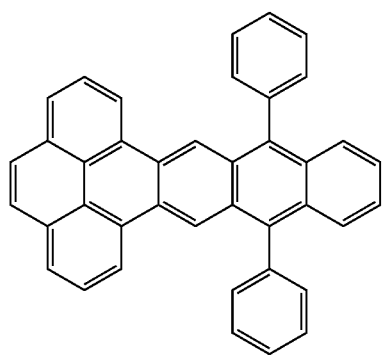
a-11
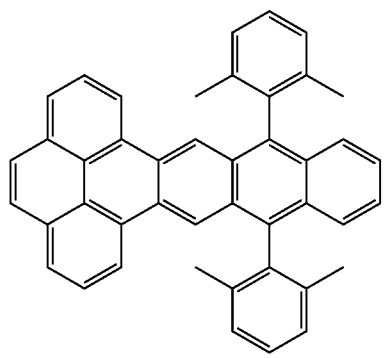
a-12
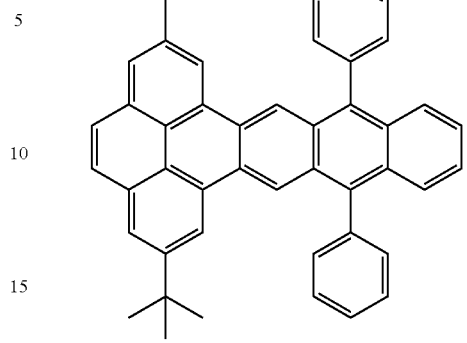
a-13
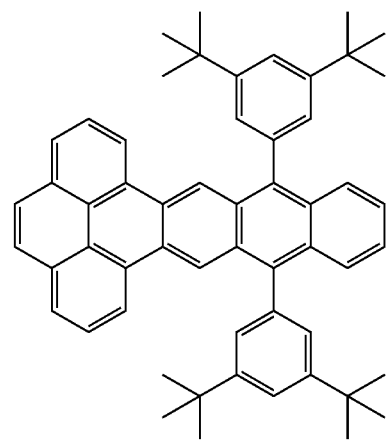
a-14
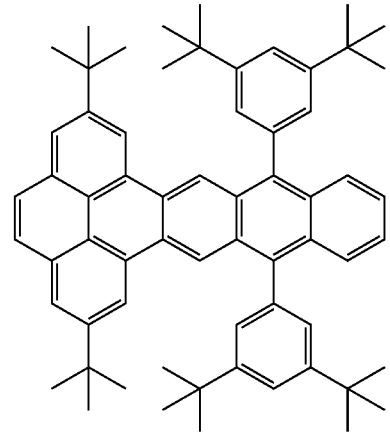
a-15
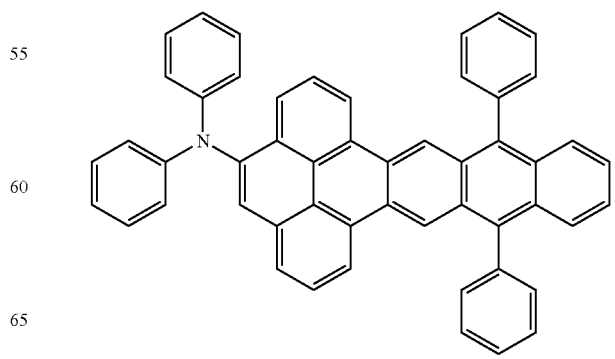

a-16 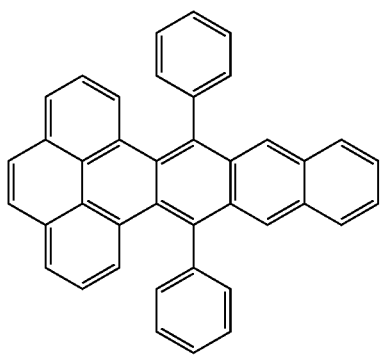
a-17 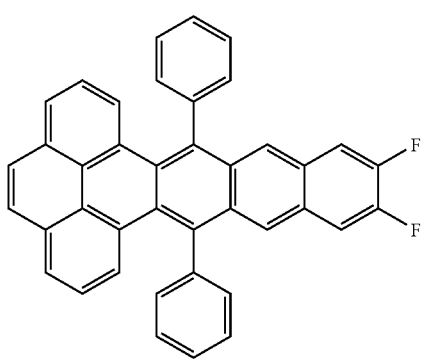
a-18 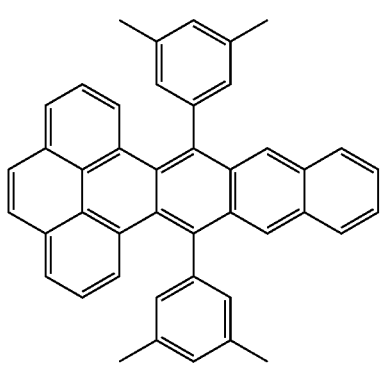
a-19 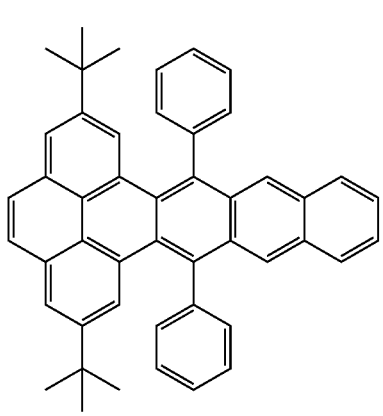
a-20 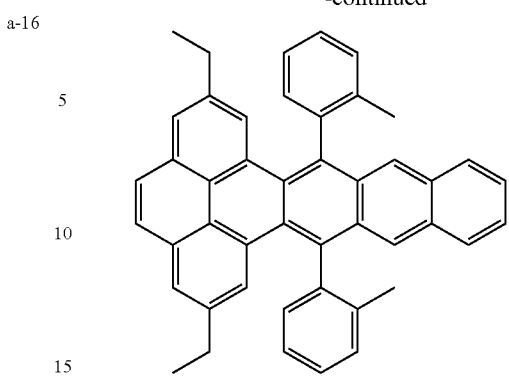
a-21 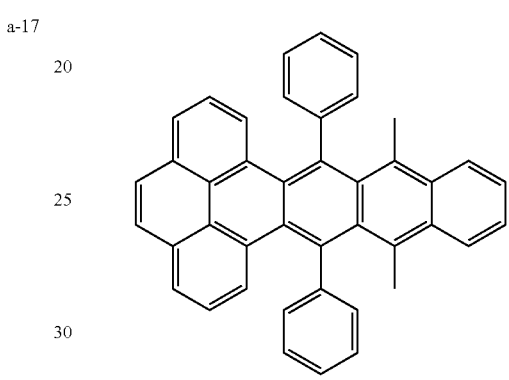
a-22 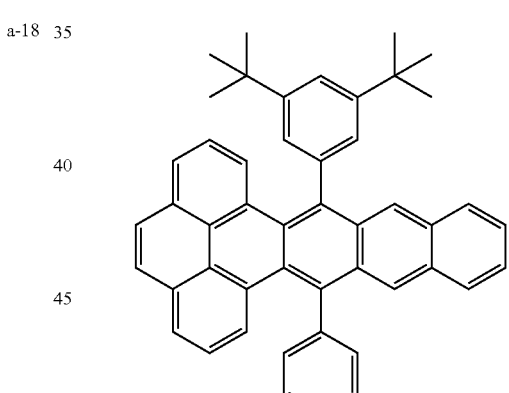
a-23 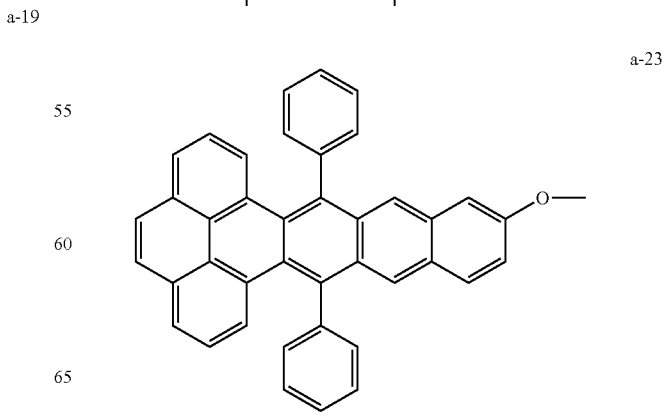

a-24
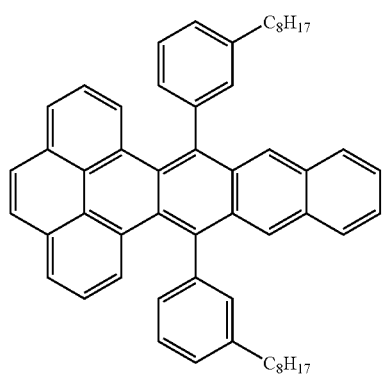
a-25
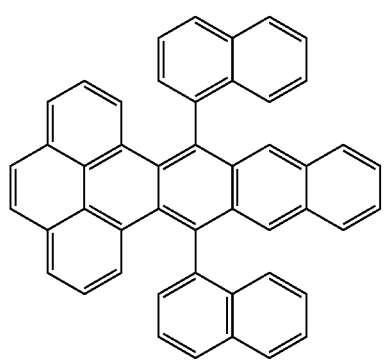
a-26
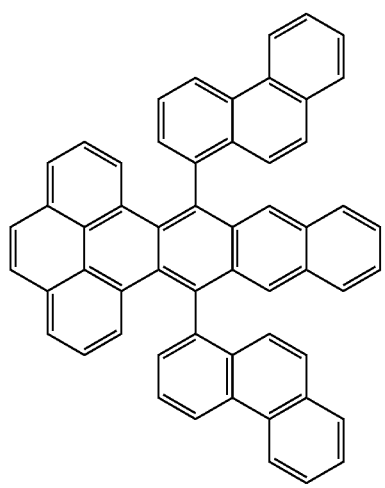
a-27
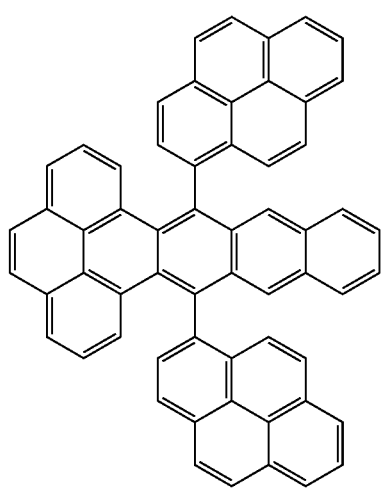
a-28
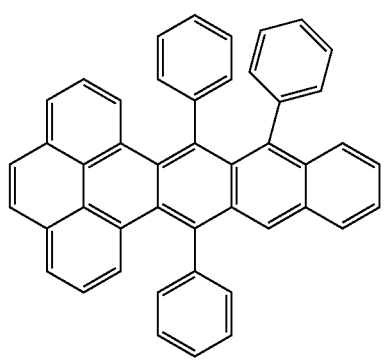
a-29
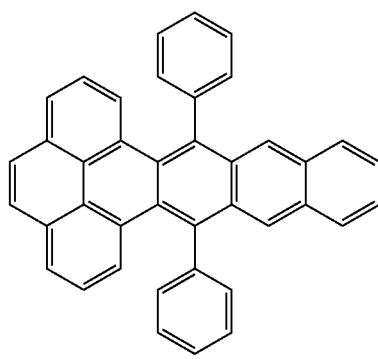
a-30
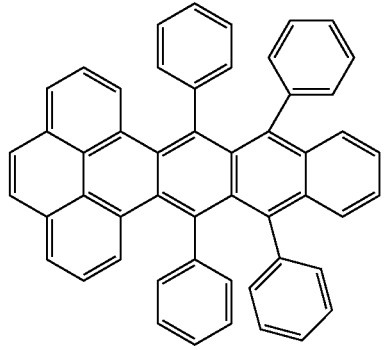

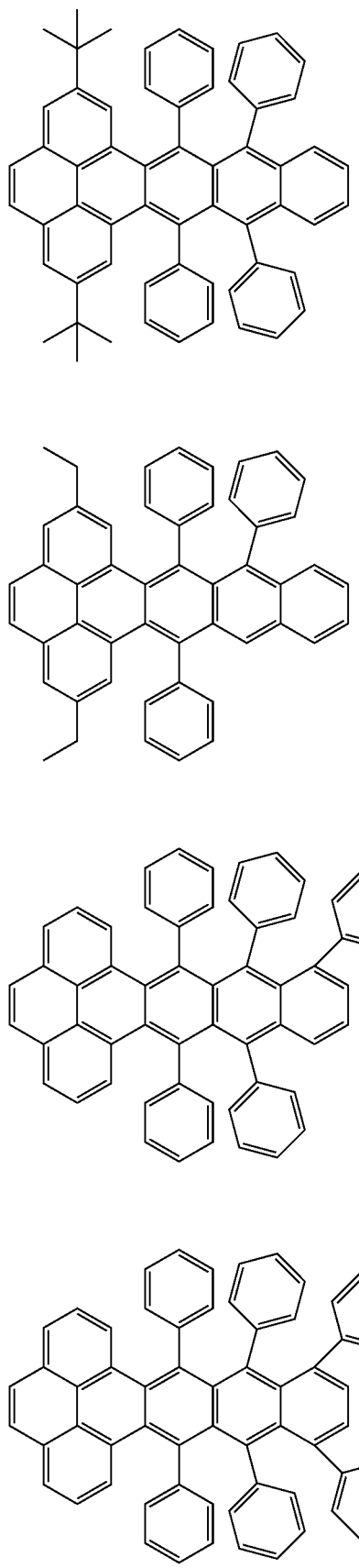
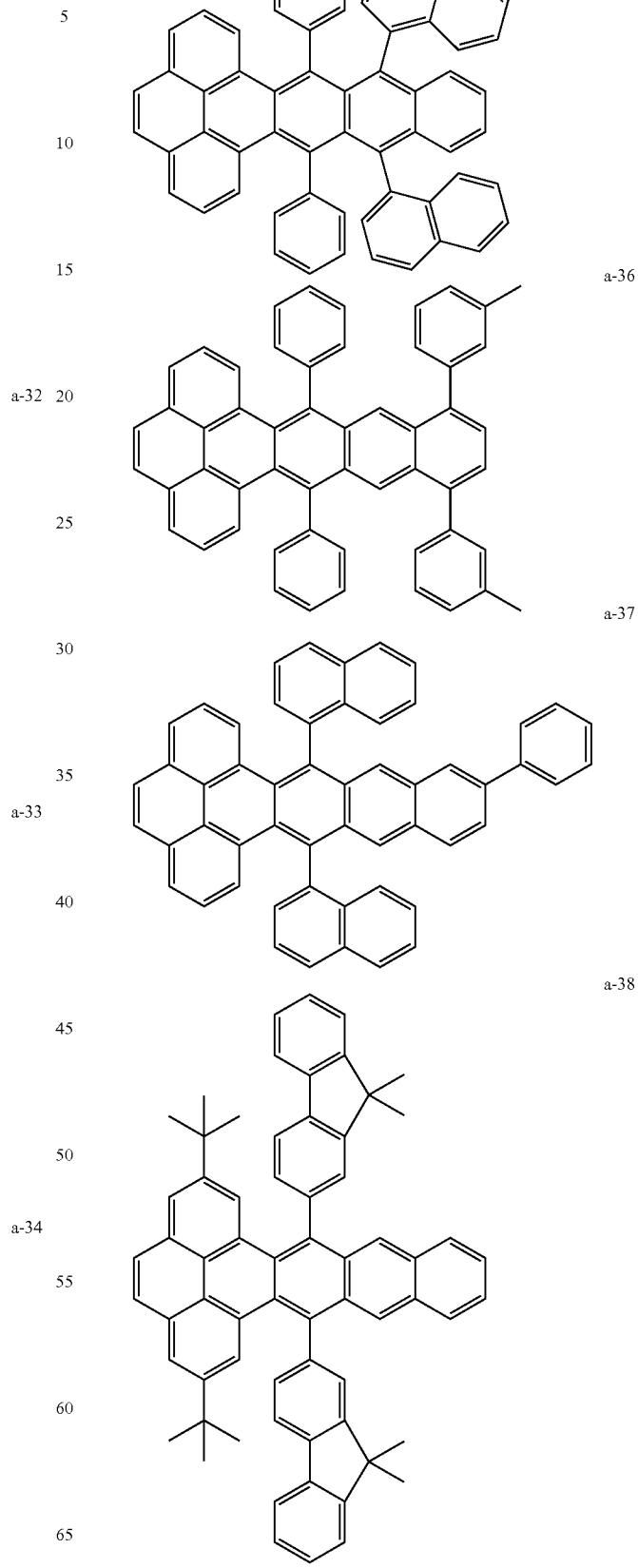

a-39
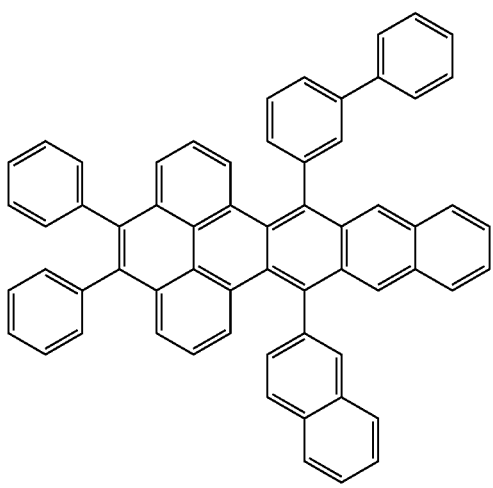
a-40
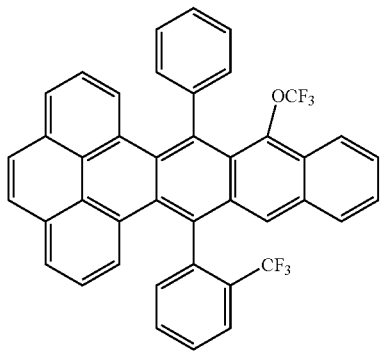
a-41
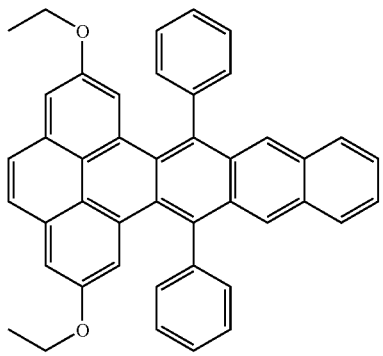
a-42
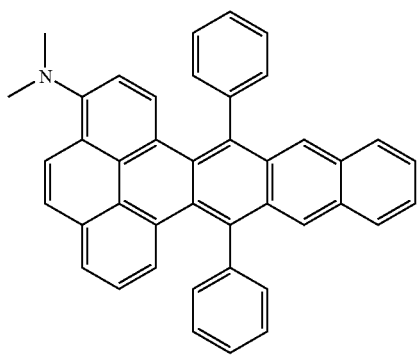
a-43
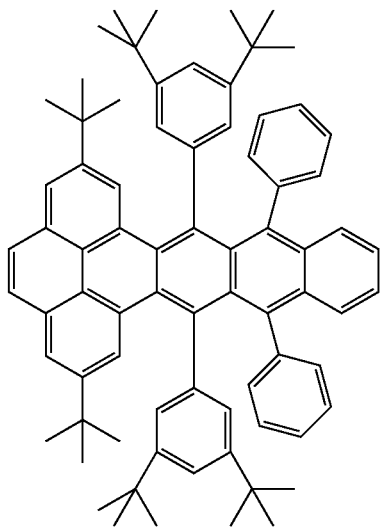
a-44
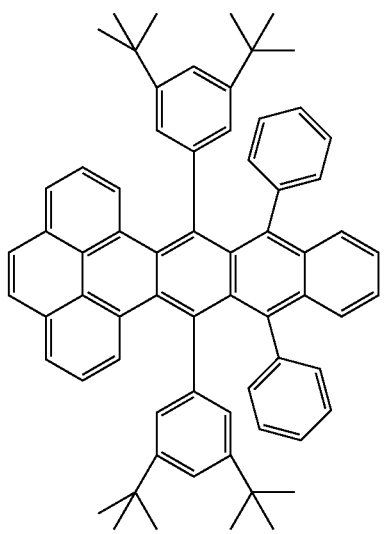
a-45
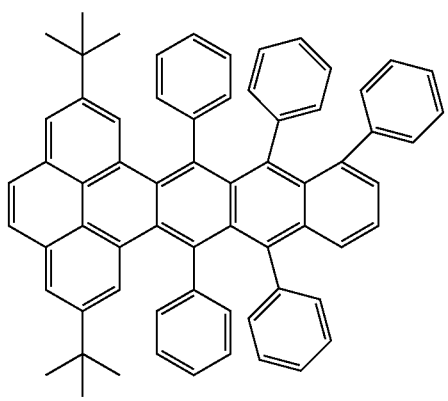

a-46
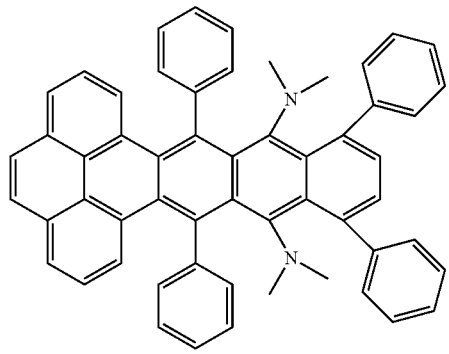
a-47
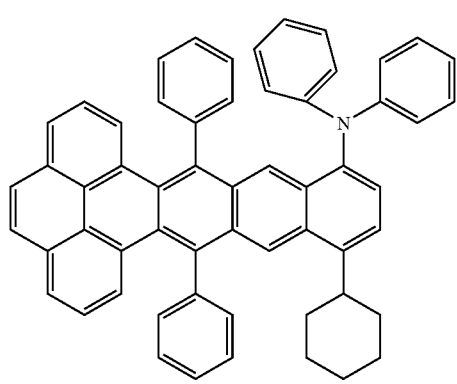
a-48
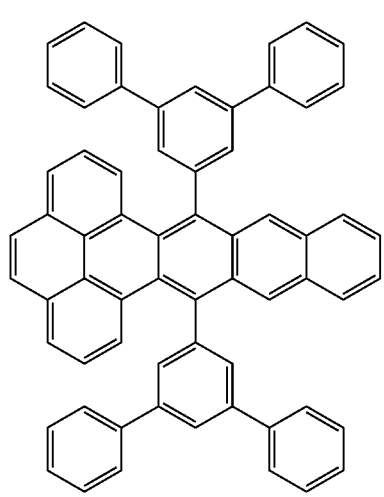
a-49
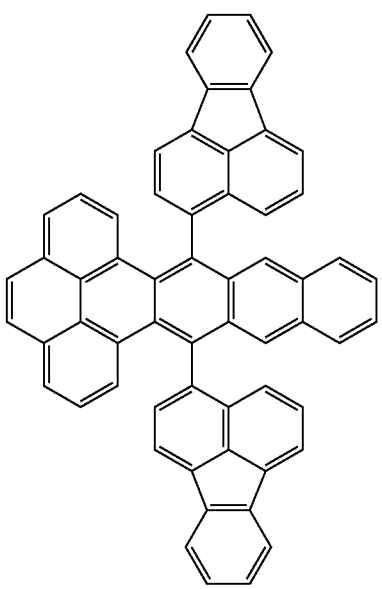
a-50
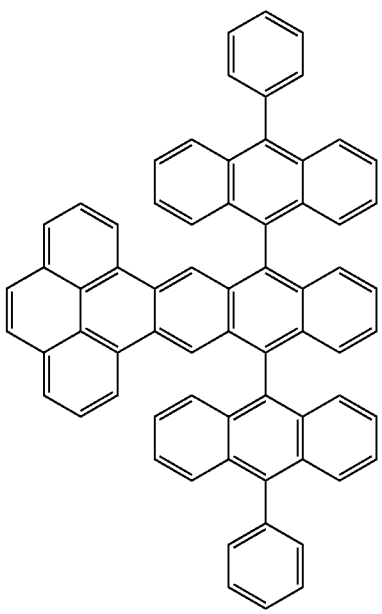

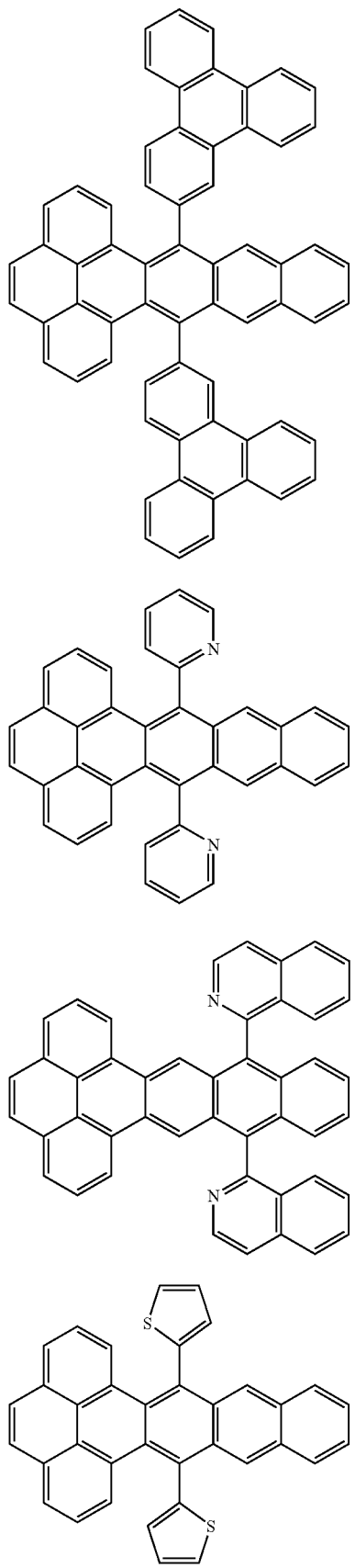
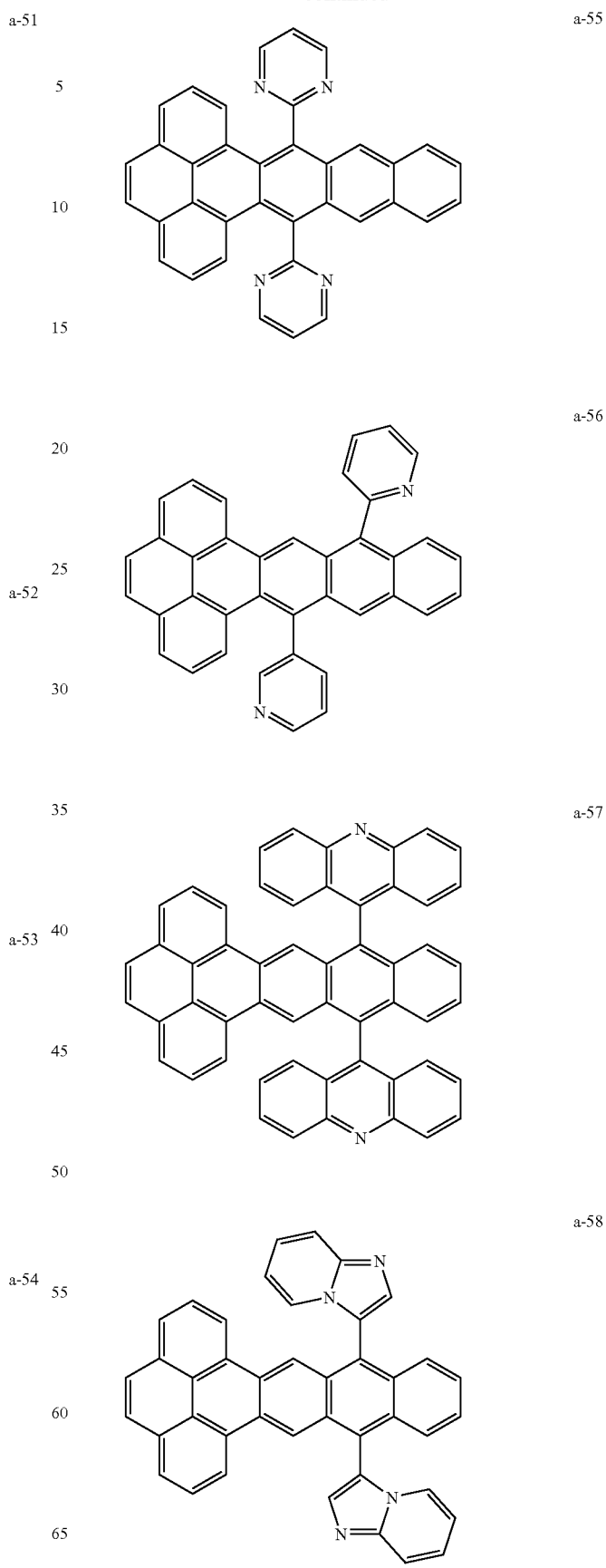

a-59
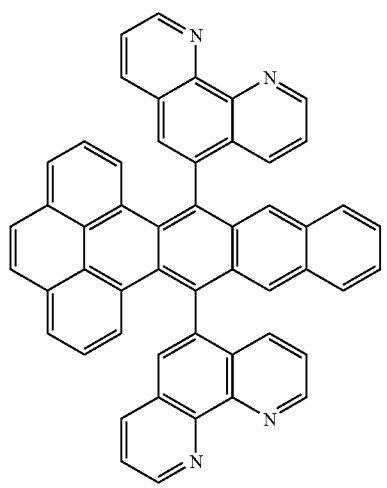
a-60
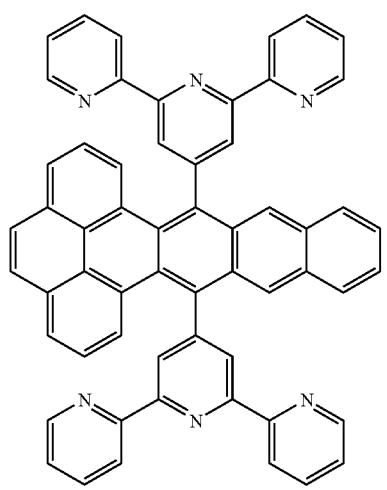
a-61
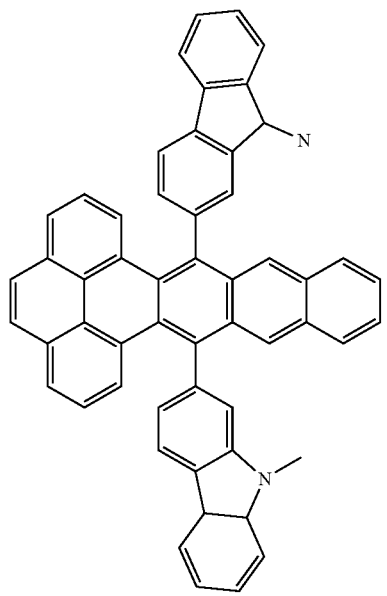
a-62
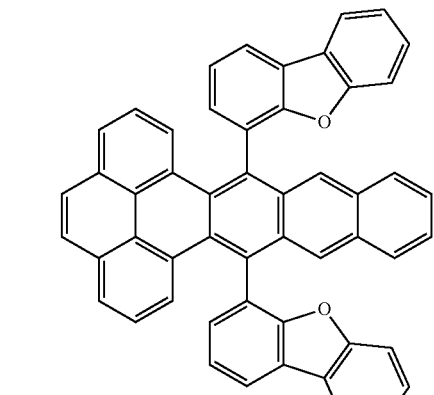
a-63
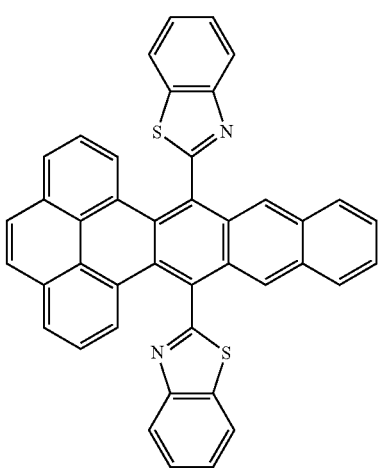
a-64
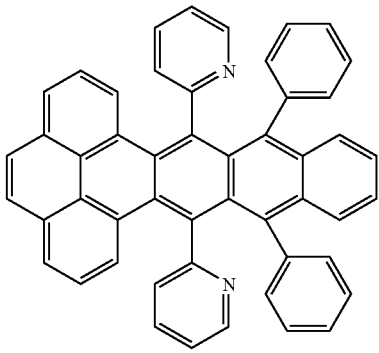
a-65
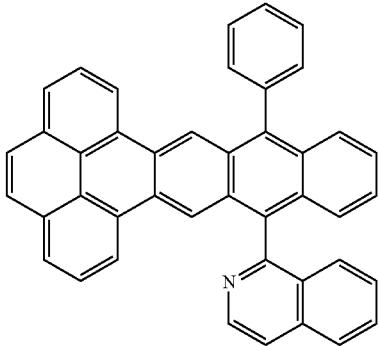

a-66
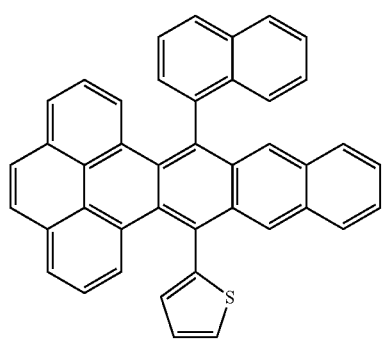
a-67
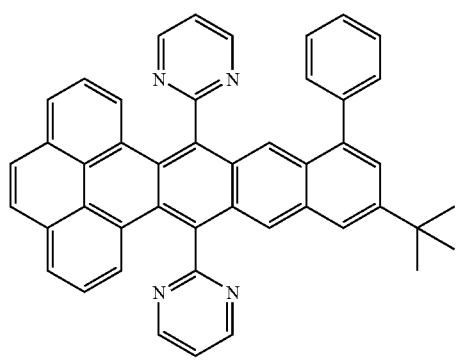
a-68
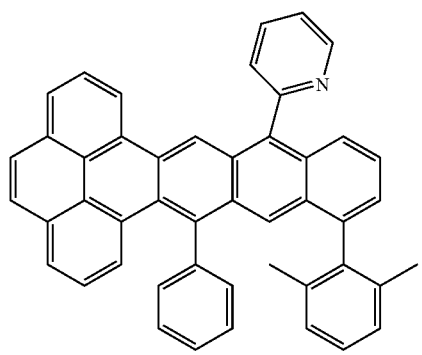
a-69
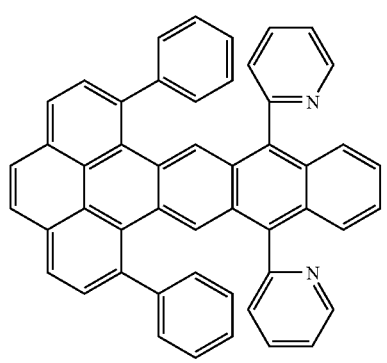
a-70
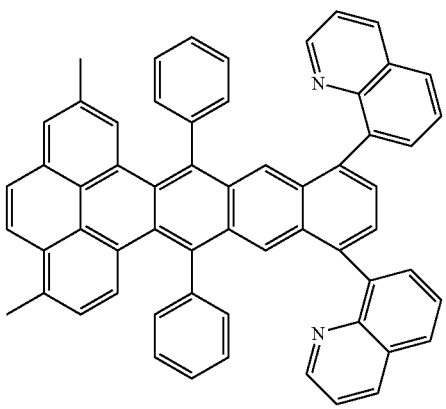
a-71
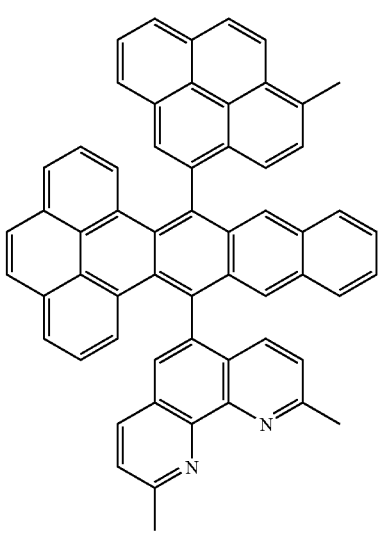
a-72
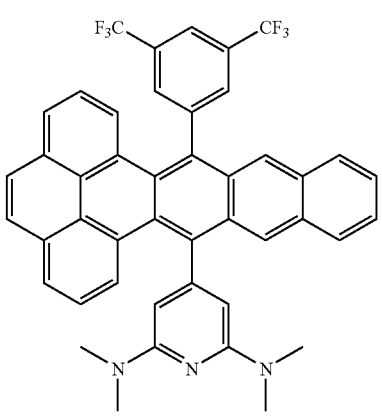

-continued

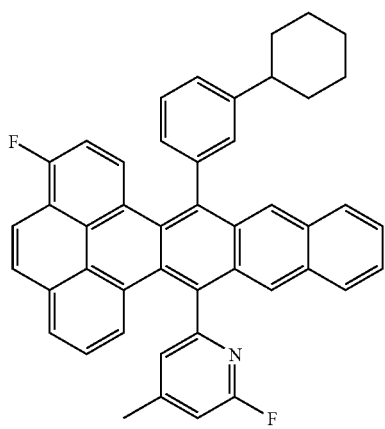
a-73

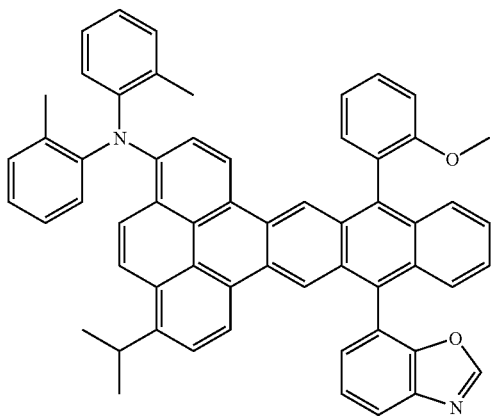
a-74

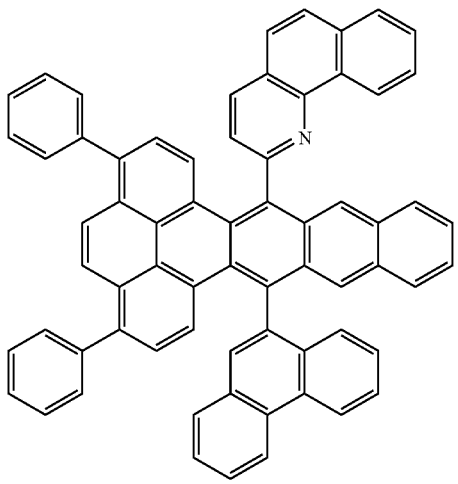
a-75

Next, an embodiment of an organic light emitting element according to the present invention will be described in detail.

The organic light emitting element of the present invention can include an anode, a cathode and a layer containing one or more organic compounds that is sandwiched between the anode and the cathode. In one version, the organic light emitting device of the present invention may be an electroluminescence device that emits a light when a voltage is applied between the anode and the cathode.

Hereinbelow, an embodiment of the organic light emitting device according to the present invention is described in detail by referring to the drawings.

First, the reference numerals in the drawings are described. Numeral 1 stands for a substrate, 2 for an anode, 3 for a light emitting layer, 4 for a cathode, 5 for a hole transport layer, 6 for an electron transport layer, 7 for a hole injection layer, 8 for a hole/exciton blocking layer, and 10, 20, 30, 40, 50 and 60 each for an organic light emitting device, respectively.

FIG. 1 is a cross-sectional view illustrating a first embodiment of an organic light emitting device according to the present invention. The organic light emitting device 10 in FIG. 1 has an anode 2, a light emitting layer 3 and a cathode 4 layered in the configuration as shown on a substrate 1. In one version, the configuration of the organic light emitting device 10 as shown may be suitable, for example, when a light emitting layer 3 is provided that includes an organic compound having all of the functions of hole transport capability, electron transport capability and light emitting capability. In another version, the configuration of the organic light emitting device 10 as shown may be suitable, for example, when it is formed from a combination of organic compounds each having at least one of the functions of hole transport capability, electron transport capability and light emitting capability.

FIG. 2 is a cross-sectional view illustrating a second embodiment of the organic light emitting device according to the present invention. The organic light emitting device 20 in FIG. 2 has an anode 2, a hole transport layer 5, an electron transport layer 6 and a cathode 4 layered in the configuration as shown on a substrate 1. In one version, this configuration of the organic light emitting device 20 may be suitable, for example, when a light emitting organic compound having either one of hole transport capability and electron transport capability, and an organic compound having only one of electron transport capability or hole transport capability, are used in combination with one another. In the organic light emitting device 20 according to this embodiment, either one of the hole transport layer 5 and the electron transport layer 6 may also function as a light emitting layer 3.

FIG. 3 is a cross-sectional view illustrating a third embodiment of an organic light emitting device according to the present invention. The organic light emitting device 30 in FIG. 3 has a light emitting layer 3 inserted between the hole transport layer 5 and the electron transport layer 6 in the organic light emitting device 20 in FIG. 2. In this embodiment of the organic light emitting device 30, the functions of carrier transportation and light emission may be separated, and therefore, in one version, this configuration of the device may be suitable when combining organic compounds each respectively having one of hole transport capability, electron transport capability and light emitting capability. Accordingly, in this embodiment, the freedom in selecting materials for the device may be increased, and various kinds of organic compounds having different emission wavelengths can be used. The embodiment may also, therefore, increase the diversity in terms of the color phase of the emitted light hue. Furthermore, in one version, the light emitting efficiency of the organic light emitting device 30 may be enhanced by effectively confining each of the carriers or excitons in the central light emitting layer 3.

Figure 4:
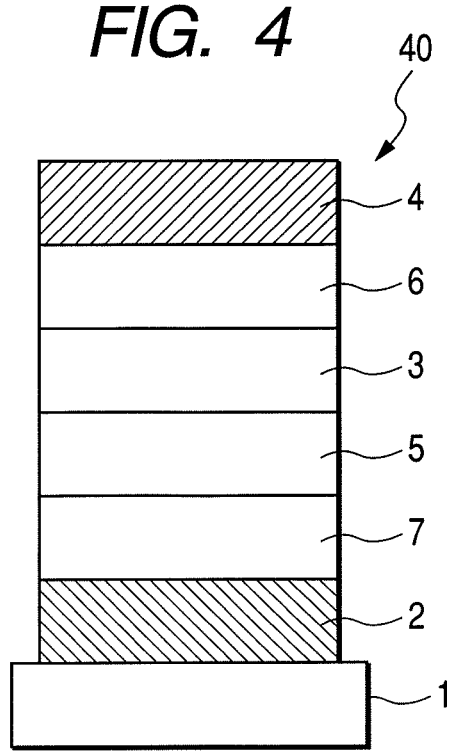
FIG. 4 is a cross-sectional view illustrating a fourth embodiment of the organic light emitting device according to the present invention.

FIG. 4 is a cross-sectional view illustrating a fourth embodiment of an organic light emitting device according to the present invention. The embodiment of the organic light emitting device 40 in FIG. 4 is modified from that shown in FIG. 3 by having a hole injection layer 7 provided between the anode 2 and the hole transport layer 5 in the organic light emitting device 30. In one version, the organic light emitting device 40 according to this embodiment having the hole injection layer 7 provides improved close contact of the anode 2 and the hole transport layer 5, thereby improving hole injection properties, and thus the device according to this embodiment may be effective for lowering the driving voltage.

Figure 5:
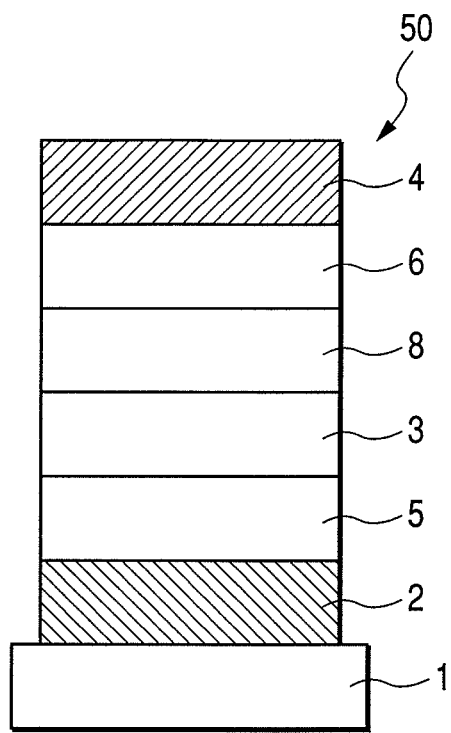
FIG. 5 is a cross-sectional view illustrating a fifth embodiment of the organic light emitting device according to the present invention.

FIG. 5 is a cross-sectional view illustrating a fifth embodiment of an organic light emitting device according to the present invention. The embodiment of the organic light emitting device 50 in FIG. 5 has a layer (hole/exciton blocking layer 8) that hinders holes or excitons from passing through to the side of the cathode 4, and is inserted at a location in the device 50 that corresponds to a location between the light emitting 3 and the electron transport layer 6 in the organic light emitting device 30 as shown in FIG. 3. In one version, the light emitting efficiency of the organic light emitting device 50 may be improved by using an organic compound having a relatively high ionization potential, and even a very high ionization potential, as a material constituting at least a portion of the hole/exciton blocking layer 8.

Figure 6:
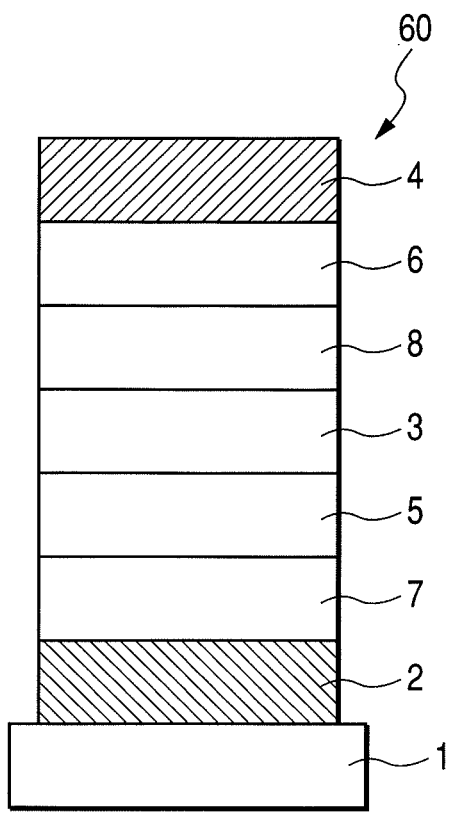
FIG. 6 is a cross-sectional view illustrating a sixth embodiment of the organic light emitting device according to the present invention.

FIG. 6 is a cross-sectional view illustrating a sixth embodiment of an organic light emitting device according to the present invention. In the version of the organic light emitting device 60 in FIG. 6, the device has a hole/exciton blocking layer 8 inserted at a location that corresponds to a location between the light emitting layer 3 and the electron transport layer 6 in embodiment of the organic light emitting device 40 shown in FIG. 4. In one version, the light emitting efficiency of the organic light emitting device 60 may be improved by using an organic compound having a relatively high ionization potential, and even a very high ionization potential, as a material constituting at least a portion of the hole/exciton blocking layer 8.

While FIGS. 1 to 6 illustrate examples of basic device constitutions, the constitution of the organic light emitting device that includes the condensed polycyclic compound according to the present invention is not intended to be limited thereto. For example, embodiments of the invention can include an insulating layer, an adhesive layer or an interfering layer provided on the interface of the electrode and the layer comprising the organic compound. Also, the hole transport layer 5 may comprise two layers having different ionization potentials.

The condensed polycyclic compound of the present invention can be used in any of the embodiments shown in FIGS. 1 to 6. In one version, the condensed polycyclic compound according to the present invention may be used as a single compound alone. In another version, the condensed polycyclic compound may be used as a combination of two or more compounds.

In one embodiment of the organic light emitting device according to the present invention, at least one condensed polycyclic compound according to the present invention is contained in a layer comprising the organic compound. The layer comprising the organic compound can comprise one or more of the light emitting layer 3, the hole transport layer 5, the electron transport layer 6, hole injection layer 7 and the hole/exciton blocking layer 8, as shown for example in FIGS. 1 to 6. For example, in one embodiment the layer comprising the organic compound may be the light emitting layer 3. In this case, the layer comprising the condensed polycyclic compound according to the present invention may comprise or consist of a single kind of the condensed polycyclic compound, or may comprise or consist of two or more kinds of the condensed polycyclic compounds in combination with each other.

In one version, when the condensed polycyclic compound of the present invention is contained in the light emitting layer 3, the light emitting layer 3 may comprise or consist of the condensed polycyclic compound of the present invention alone. However, the layer 3 may also comprise both a host and a guest.

In one embodiment, when the condensed polycyclic compound of the present invention is used as a host in the light emitting layer 3, the light emitting material that serves as a guest may not be limited but may be, for example, a fluorescent material. When the condensed polycyclic compound of the present invention is used as a host in the light emitting layer 3, the content thereof may be, for example, 50% by weight or more and 99.9% by weight or less, such as 80% by weight or more and 99.9% by weight or less based on the total weight of the materials constituting the light emitting layer 3.

When the condensed polycyclic compound of the present invention is used as a guest (light emitting material) in the light emitting layer 3, the content thereof may be, for example 0.1% by weight or more and 50% by weight or less, such as 0.1% by weight or more and 20% by weight or less based on the total weight of the materials constituting the light emitting layer 3. Specific examples of a corresponding host are described later.

In one embodiment, the condensed polycyclic compound according to the present invention can be incorporated into any layer, as long as the layer comprises an organic compound and forms a portion of an organic light emitting device. Also, a hole transporting material, a host, a light emitting material and an electron transporting material can be suitably used in combination with the condensed polycyclic compound according to the present invention.

Examples of the hole transporting material include the compounds represented by the following formulas.

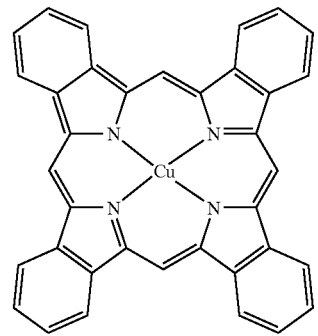

XA-1

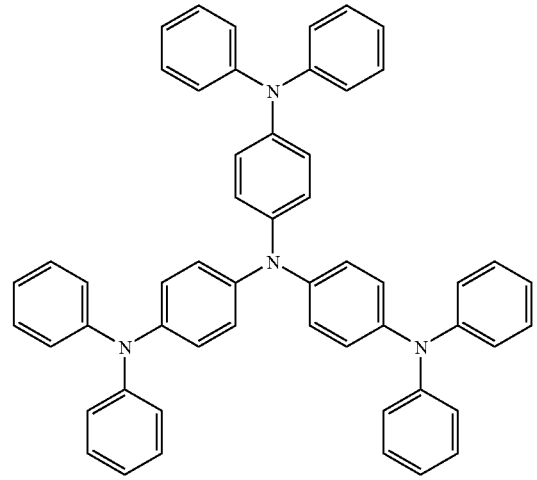

XA-2

-continued
XA-3
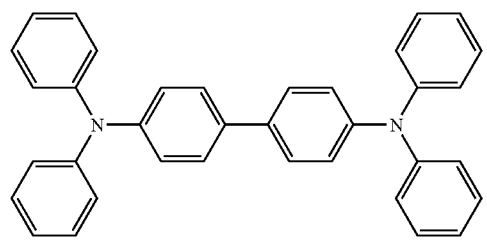
XA-4
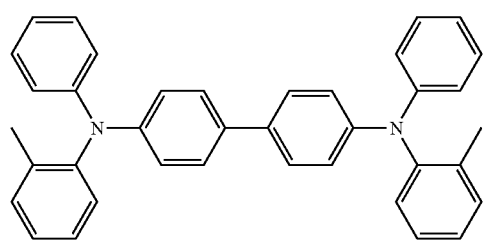
XA-5
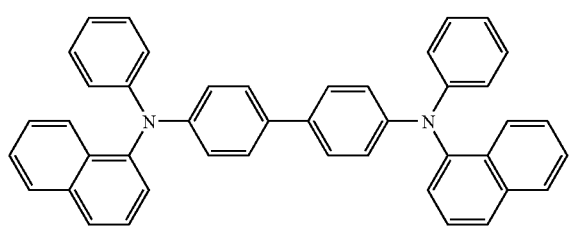
XA-6
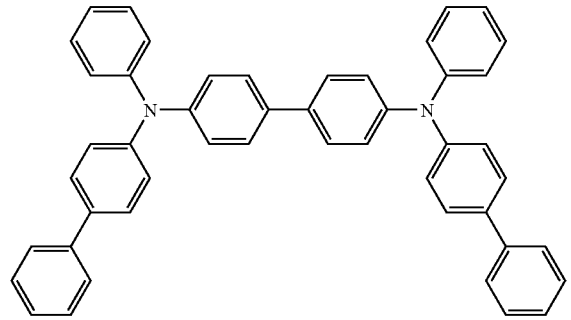
XA-7
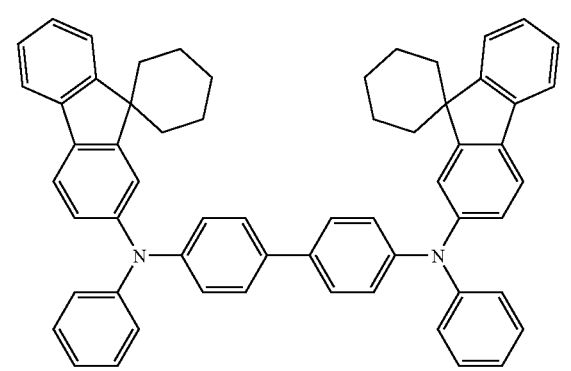
XA-8
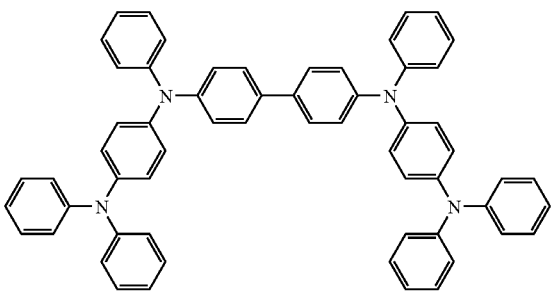
XA-9
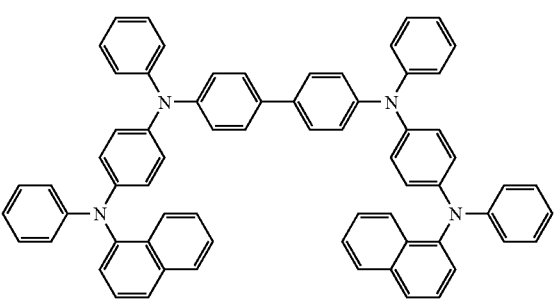
XA-10
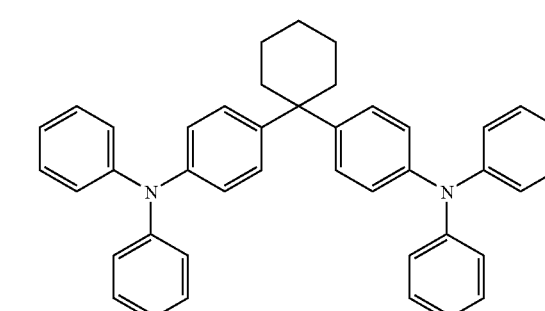
XA-11
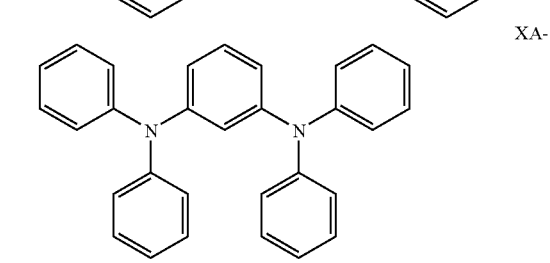
XA-12
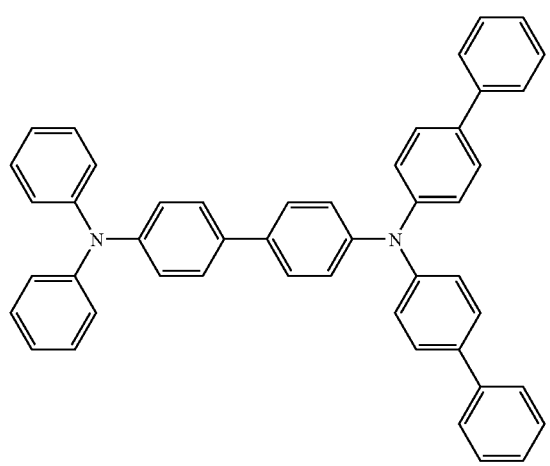

Examples of the host include the compounds represented by the following formulas.
XB-1
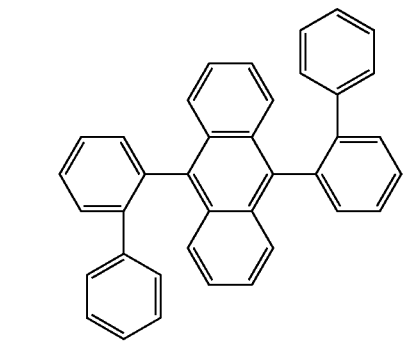
XB-2
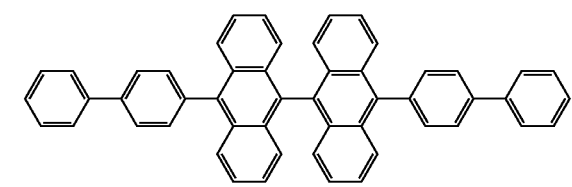
XB-3
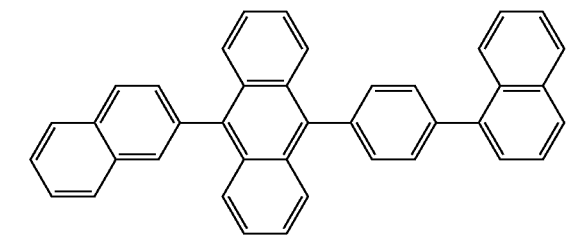
XB-4
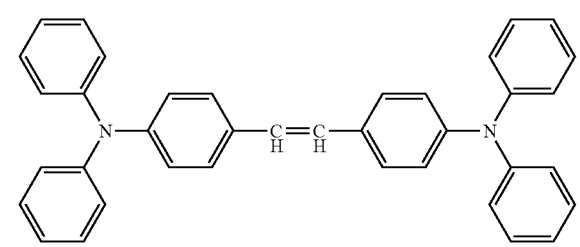
XB-5
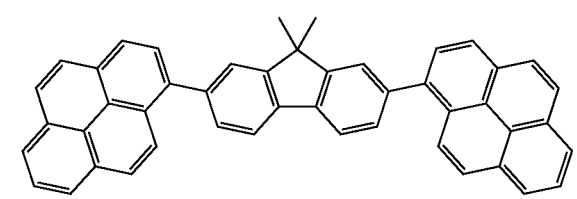
XB-6
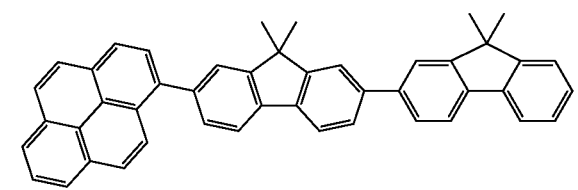
XB-7
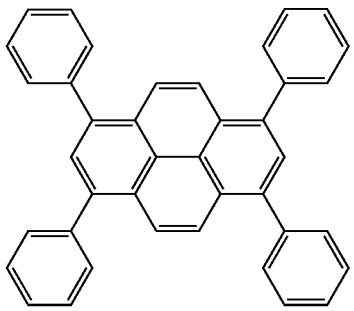
XB-8
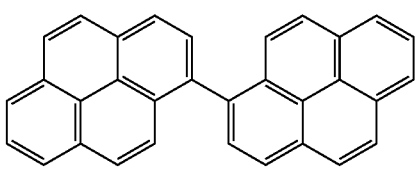
XB-9
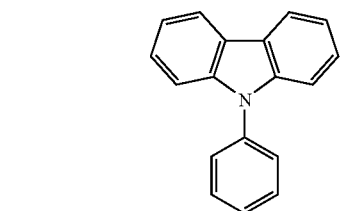
XB-10
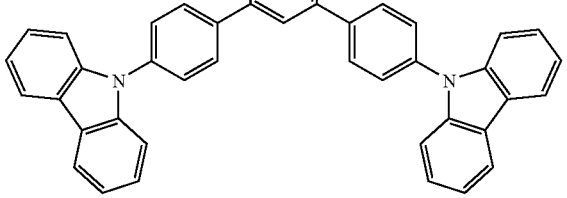
XB-10
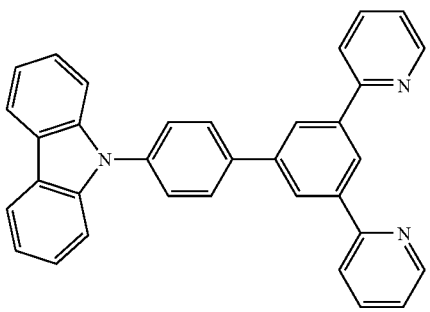
XB-11
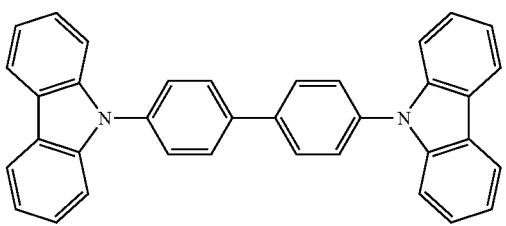

XB-12
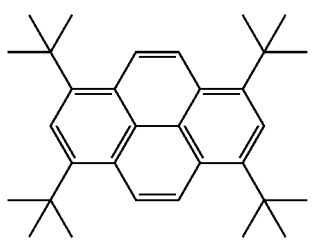
Examples of light emitting materials other than the condensed polycyclic compound according to the present invention include the compounds represented by the following formulas.
XC-1
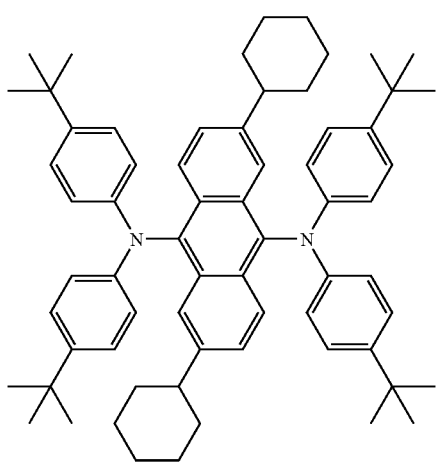
XC-2
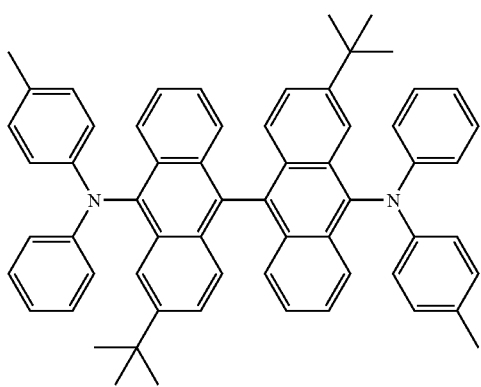
XC-3
XC-4
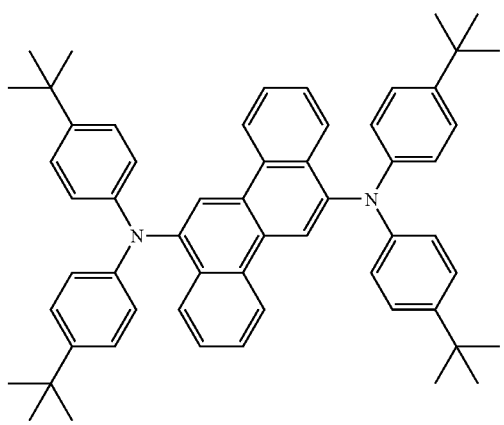
XC-5
XC-6
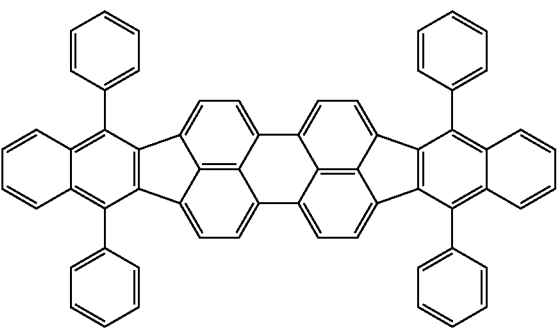
XC-7
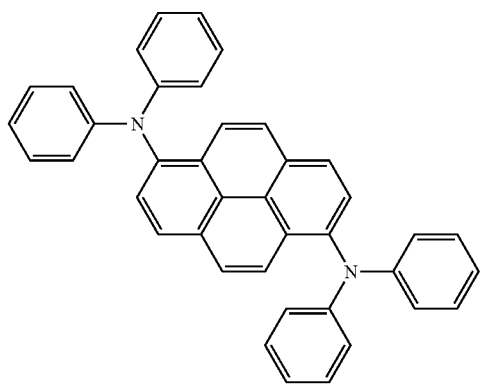

XC-8
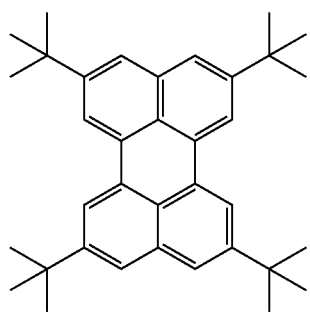
XC-9
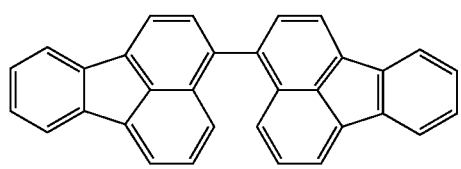
XC-10
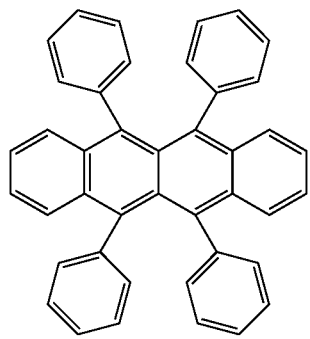
XC-11
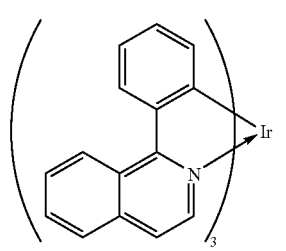
XC-12
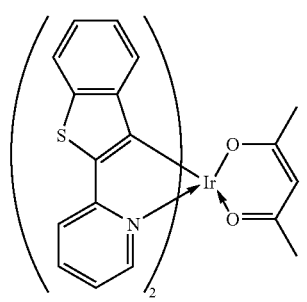
Examples of electron transporting materials include compounds represented by the following formulas.
XD-1
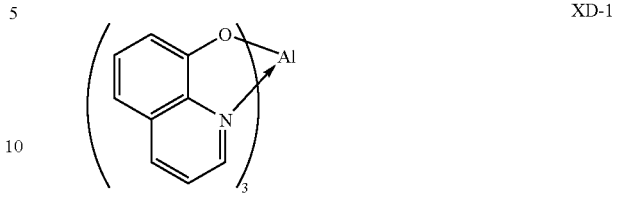
XD-2
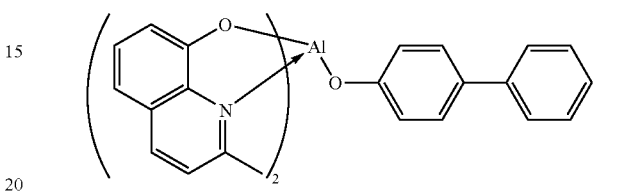
XD-3
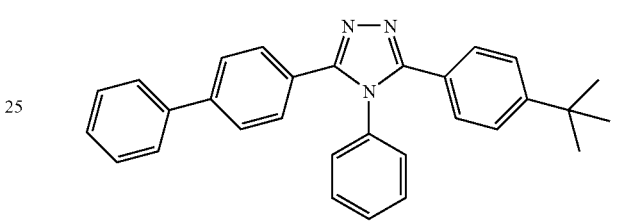
XD-4
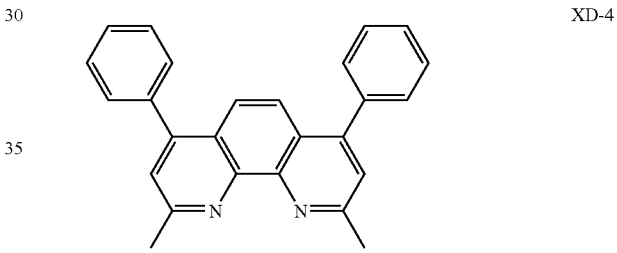
XD-5
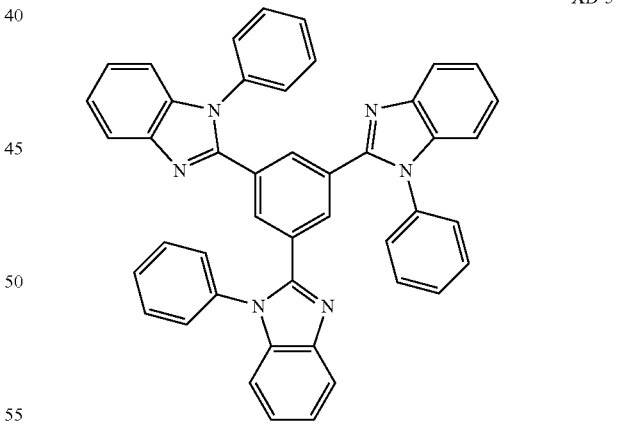
XD-6
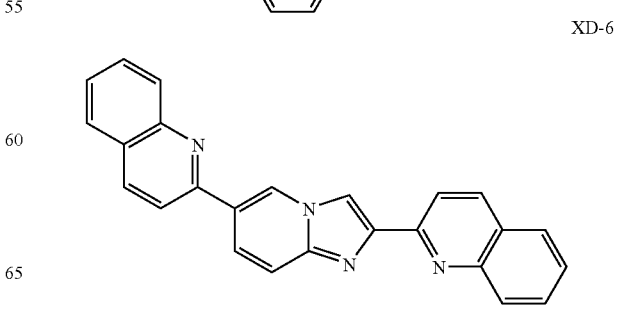

As anode materials for the organic light device of the present invention, suitable materials may be those having a relatively high work function, and even a work function that is as high as possible. For example, simple metal substances such as gold, platinum, nickel, palladium, cobalt, selenium and vanadium, alloys combining these or metal oxide such as tin oxide, zinc oxide, indium tin oxide (ITO) and indium zinc oxide can be used. In addition, conductive polymers such as polyaniline, polypyrrol, polythiophene and polyphenylene sulfide can be used. These electrode materials may be used as a single kind of substance alone, or two or more kinds of the substances may be used in combination.

On the other hand, as cathode materials for the organic light device of the present invention, suitable materials may be those having a relatively low work function, and even those having as low a work function as possible. Examples thereof include simple metal substances such as lithium, sodium, potassium, cesium, calcium, magnesium, aluminum, indium, silver, lead, zinc and chromium and alloys combining these can be used. Use of metal oxides such as indium tin oxide (ITO) may also be possible. In one version, the cathode may consist of one layer, or alternatively the cathode may consist of two or more layers.

The type of substrate usable in the organic light emitting device of the present invention is not particularly limited, and non-transparent substrates such as metal substrates and substrates made of ceramics and transparent substrates such as glass, quartz and plastic sheets, may also be used. In one version, the color of the emitting light can be controlled using, for example, a color filter film, a fluorescent color conversion filter film, a dielectric reflection film, etc., on the substrate.

In addition, in one version, a protective layer or a sealing layer can be provided on the organic light emitting devices for the purpose of reducing and even preventing exposure to oxygen or moisture. Examples of the protective layer may include inorganic material films such as a diamond film, metal oxides and metal nitrides, polymer films such as fluoric resins, polyparaxylene, polyethylene, silicone resins and polystyrene resins, and further light curing resins. The substrates may also be covered with glass, a gas impermeable film and a metal, and the device itself may be packaged in a suitable sealing resin.

In one version, when the organic light emitting device according to the present invention is prepared, the layer containing an organic compound including the condensed polycyclic compound of the present invention can be film formed by, for example, a vacuum deposition method, cast method, coating method, spin coating, ink-jet method, etc. The other layers can be prepared in a similar manner.

EXAMPLES

Hereinbelow the present invention is specifically described by way of working examples. However, the present invention is not intended to be limited thereto.

Example 1

Synthesis of Example Compound a-16

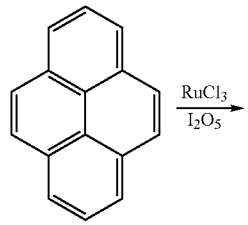

XX-1

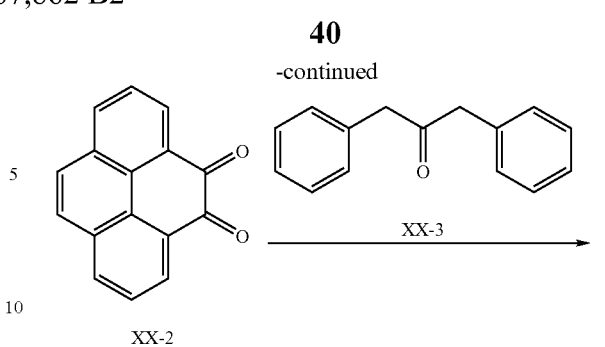

XX-2

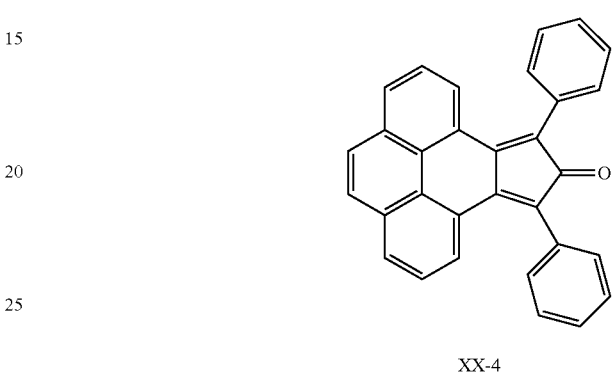

XX-4

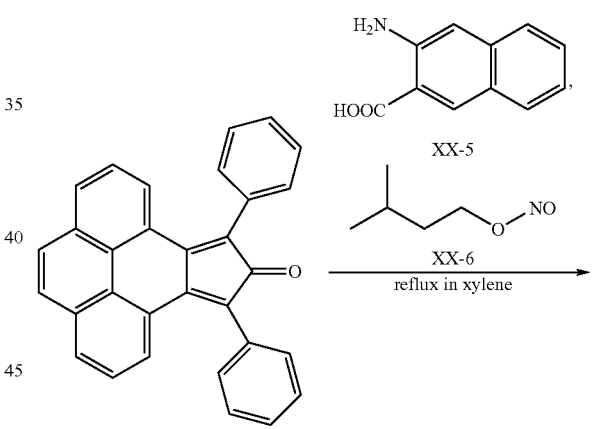

XX-4

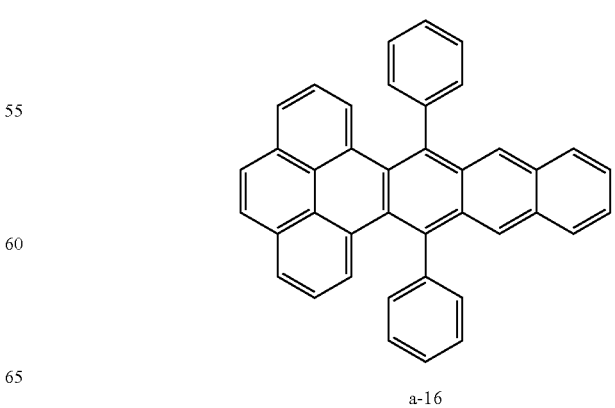

a-16

(1) Intermediate Compound XX-4 was synthesized from pyrene (Compound XX-1) following the method described in, for example, J. Org. Chem., 70, 707 (2005) and J. Am. Chem. Soc., 109, 4660 (1987).

(2) Reagents and a solvent shown below were placed in a reaction container having a volume of 30 ml.
Intermediate Compound XX-4: 406 mg (1.0 mmol)
Compound XX-5: 374 mg (2.0 mmol)
Isoamyl nitrite (Compound XX-6): 403 µl (3.0 mmol)
Xylene: 10 mL Subsequently, the reaction solution was stirred for three hours while heating to reflux. Then, the reaction solution was cooled to room temperature and after that, 20 ml of a saturated saline solution was added and then the organic layer was extracted by chloroform (15 mL×3 times). Then, the organic layer was washed with a saturated saline solution and after that, dried over sodium sulphate. Subsequently, the mixture was subjected to filtration to separate the desiccating agent and the filtrate and after that, the filtrate was vacuum concentrated. Subsequently, the product was purified by silica gel column chromatography (mobile phase; toluene:hexane=1: 3) to obtain crude yellow crystals. 257 mg of Example Compound a-16 (yield 51%) was obtained by recrystallizing these crude yellow crystals from a mixed toluene-hexane solvent.

The obtained compound was subjected to electronic ionization mass spectrum (EI-MS) measurement and 504, M+ of this compound, was confirmed. The obtained compound was also subjected to NMR measurement. The results of the measurement are shown below.

$^1$H-NMR (CDCl$_3$, 500 MHz) σ (ppm): 8.49 (s, 2H), 7.90 (m, 2H), 7.85 (s, 2H), 7.81 (d, 2H), 7.75 (d, 2H), 7.63 (m, 4H), 7.56 (m, 6H), 7.42 (m, 2H), 7.30 (t, 2H).

Example 2

An organic light emitting device having a layer containing an organic compound that is composed of three layers (i.e. an electron transport layer 6, light emitting layer 3 and hole transport layer 5), as shown in FIG. 3, was prepared.

At first, a transparent substrate with ITO electrodes was prepared by forming an anode 2 by patterning indium tin oxide (ITO) on a glass substrate (substrate 1). The film thickness of the anode 2 was 100 nm and the electrode area was 3 mm$^2$. Then, a layer containing an organic compound and a cathode were successively film formed on the transparent substrate with ITO electrodes by vacuum vapor deposition by resistance heating. The pressure in a vacuum chamber was 10$^{-5}$ Pa. Specifically, α-NPD shown below was vapor deposited to form a hole transport layer 5. The film thickness of the hole transport layer 5 was 40 nm. Then, HOST-1 shown below, which is a host, and Example Compound a-16, which is a guest, were co-vapor-deposited to form a light emitting layer 3 so that the content of the guest (Example Compound a-16) was 5% by weight of the entire materials constituting the light emitting layer 3. The film thickness of the light emitting layer 3 was 30 nm. Then, Bphen (produced by Dojindo Laboratories) shown below was vapor deposited to form an electron transport layer 6. The film thickness of the electron transport layer 6 was 30 nm. Then, KF was vapor deposited to form a first metal electrode layer. The film thickness of the first metal electrode layer was 1 nm. Finally, Al was vapor deposited to form a second metal electrode layer. The film thickness of the second metal electrode layer was 130 nm. The KE film and the Al film function together as a cathode 4. As above, an organic light emitting device was obtained.

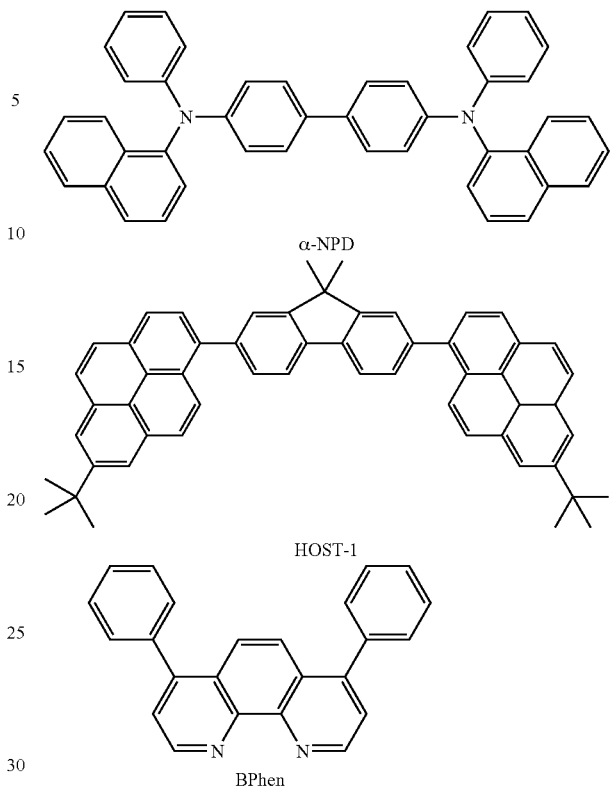

α-NPD

HOST-1

BPhen

When a voltage was applied to the device of this embodiment in a nitrogen atmosphere for 100 hours, continuation of the good light emission was confirmed. In addition, the device of this embodiment emitted green light when voltage was applied thereto, and therefore, it was confirmed that Example Compound a-16 is useful as a green light emitting material.

Example 3

An organic light emitting device having a layer containing an organic compound that is composed of four layers (i.e., an electron transport layer 6, light emitting layer 3, hole transport layer 5 and hole injection layer 7), as shown in FIG. 4, was prepared.

At first, a transparent substrate with ITO electrodes was prepared by forming an anode 2 by patterning indium tin oxide (ITO) on a glass substrate (substrate 1). The film thickness of the anode 2 was 100 nm and the electrode area was 3 mm$^2$. Then, the layer containing the organic compound and a cathode layer were successively film formed on the transparent substrate with ITO electrodes by vacuum vapor deposition by resistance heating. The pressure in a vacuum chamber was 10$^{-5}$ Pa. Specifically, α-NPD shown below was vapor deposited to form a hole injection layer 7. The film thickness of the hole injection layer 7 was 20 nm. Then, Example Compound a-16 was vapor deposited to form a hole transport layer 5. The film thickness of the hole transport layer 5 was 40 nm. HOST-1, which is a host, and GUEST-1 shown below, which is a guest, were co-vapor-deposited to form a light emitting layer 3 so that the content of the guest (GUEST-1) was 10% by weight of the entire materials constituting the light emitting layer 3. The film thickness of the light emitting layer 3 was 30 nm. Then, Bphen (produced by Dojindo Laboratories) shown below was vapor deposited to form an electron transport layer 6. The film thickness of the electron transport layer 6 was 30 nm. Then, KF was vapor deposited to form a first metal electrode layer. The film thickness of the first metal electrode layer was 1 nm. Finally, Al was vapor deposited to form a second metal electrode layer. The film thickness of the second metal electrode layer was 130 nm. The KF film and the Al film function together as a cathode 4. As above, an organic light emitting device was obtained.

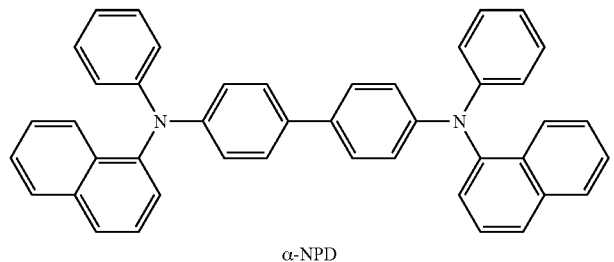
α-NPD

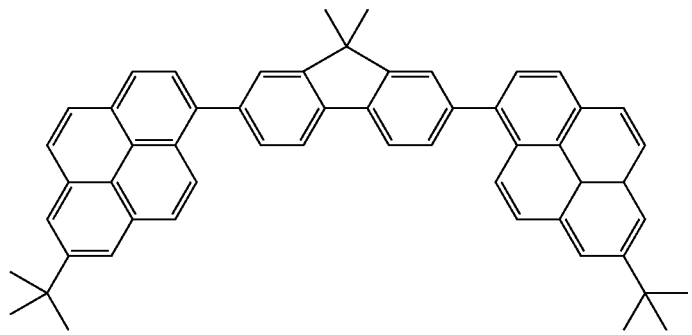
HOST-1

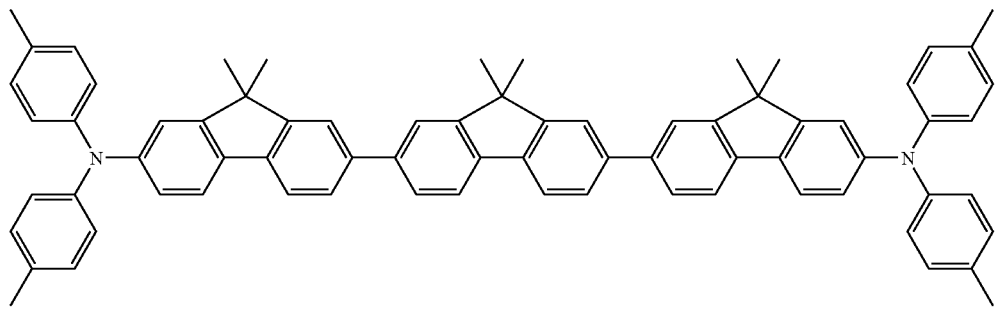
GUEST-1

When a voltage was applied to the device of this embodiment in a nitrogen atmosphere for 100 hours, continuation of the good light emission was confirmed.

Accordingly, the organic light emitting devices according to these examples exhibit good durability. The organic light emitting devices according to these examples may also be fairly easily prepared at a relatively low cost. Accordingly, the light emitting devices may be excellent for use in a display device.

While the present invention has been described with reference to exemplary embodiments, it is to be understood that the invention is not limited to the exemplary embodiments disclosed herein. Accordingly, the scope of the following claims is to be accorded the broadest interpretation so as to encompass all such modifications and equivalent structures and functions.

This application claims the benefit of Japanese Patent Application No. 2007-286105, filed Nov. 2, 2007, which is hereby incorporated by reference herein in its entirety.

What is claimed is:

1. An organic light emitting device comprising:
an anode and a cathode; and
a light emitting layer disposed between the anode and the cathode,
wherein the light emitting layer comprises a host material and a guest material;
the guest material is a fluorescent material,
the host material is a condensed polycyclic compound represented by the following Formula [1]:

[1]
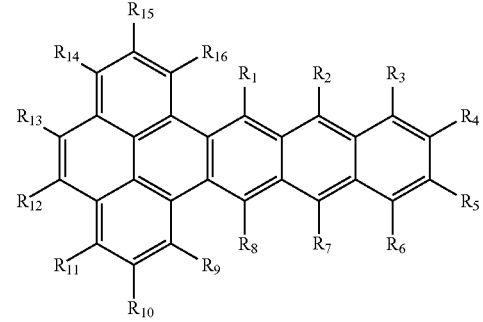

wherein in Formula [1], $R_1$ to $R_{16}$ each represent a hydrogen atom, a halogen atom, an alkyl group having 1 to 20 carbon atoms, a substituted amino group, an aryl group that may optionally have a substituent group, or a heterocyclic group that may optionally have a substituent group, provided that at least one of $R_1$, $R_2$, $R_7$ and $R_8$ is an aryl group that may optionally have a substituent group, or a heterocyclic group that may optionally have a substituent group.

2. The organic light emitting device according to claim 1, wherein the guest material is at least one of organic compounds represented by following structure.

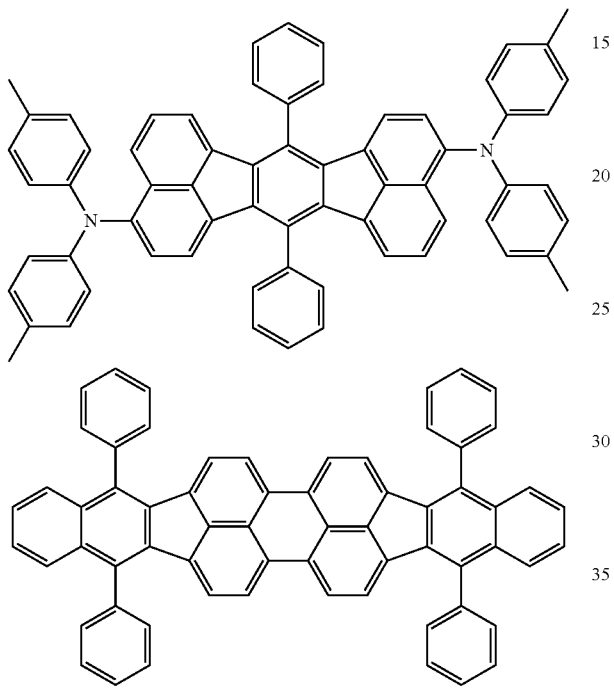

3. An organic light emitting device comprising:
an anode and a cathode; and
a layer comprising an organic compound disposed between the anode and the cathode, wherein the layer comprising a hole transporting layer,
the hole transporting layer comprising a condensed polycyclic compound represented by the following Formula [1]

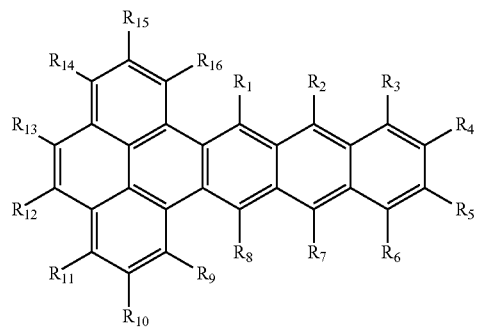

[1]

wherein in Formula [1], $R_1$ to $R_{16}$ each represent a hydrogen atom, a halogen atom, an alkyl group having 1 to 20 carbon atoms, a substituted amino group, an aryl group that may optionally have a substituent group, or a heterocyclic group that may optionally have a substituent group, provided that at least one of $R_1$, $R_2$, $R_7$ and $R_8$ is an aryl group that may optionally have a substituent group, or a heterocyclic group that may optionally have a substituent group.

4. An apparatus comprising:
a substrate and an organic light emitting device according to claim 1, and
a color filter.

5. The organic light emitting device according to claim 1, wherein the R1 and R8 are each independently selected from the aryl group.

6. The organic light emitting device according to claim 5, wherein the R2 and R7 are each independently selected from the aryl group.

* * * * *